US012716092B2

(12) United States Patent
Costa

(10) Patent No.: US 12,716,092 B2

(45) Date of Patent: Aug. 25, 2026

(54) METHOD OF IDENTIFYING CIRCULAR RNA

(71) Applicant: 10x Genomics, Inc., Pleasanton, CA (US)

(72) Inventor: Justin Costa, Union City, CA (US)

(73) Assignee: 10X GENOMICS, INC., South San Francisco, CA (US)

( * ) Notice: Subject to any disclaimer, the term of this patent is extended or adjusted under 35 U.S.C. 154(b) by 544 days.

(21) Appl. No.: 18/320,097

(22) Filed: May 18, 2023

(65) Prior Publication Data

US 2023/0374580 A1 Nov. 23, 2023

Related U.S. Application Data

(60) Provisional application No. 63/343,922, filed on May 19, 2022.

(51) Int. Cl.

*C12Q 1/6865* (2018.01)
*C12Q 1/44* (2006.01)
*C12Q 1/6841* (2018.01)

(52) U.S. Cl.

CPC ............ *C12Q 1/6865* (2013.01); *C12Q 1/44* (2013.01); *C12Q 1/6841* (2013.01)

(58) Field of Classification Search

CPC ...... C12Q 1/6865; C12Q 1/44; C12Q 1/6841; C12Q 1/6844

See application file for complete search history.

(56) References Cited

U.S. PATENT DOCUMENTS

| | | | |
|---|---|---|---|
| 4,318,846 | A | 3/1982 | Khanna et al. |
| 4,683,195 | A | 7/1987 | Mullis et al. |
| 4,683,202 | A | 7/1987 | Mullis |
| 4,757,141 | A | 7/1988 | Fung et al. |
| 4,800,159 | A | 1/1989 | Mullis et al. |
| 4,849,336 | A | 7/1989 | Miyoshi et al. |
| 4,965,188 | A | 10/1990 | Mullis et al. |
| 5,066,580 | A | 11/1991 | Lee |
| 5,091,519 | A | 2/1992 | Cruickshank |

(Continued)

FOREIGN PATENT DOCUMENTS

| | | | |
|---|---|---|---|
| IN | 201931015071 A * | 10/2020 | .......... C12Q 1/6844 |
| WO | WO 2017/143155 | 8/2017 | |

(Continued)

OTHER PUBLICATIONS

Zaghlool, A., Ameur, A., Wu, C. et al. Expression profiling and in situ screening of circular RNAs in human tissues. Sci Rep 8, 16953 (2018). https://doi.org/10.1038/s41598-018-35001-6 (Year: 2018).*

(Continued)

*Primary Examiner* — Samuel C Woolwine
*Assistant Examiner* — Kara N Kovach
(74) *Attorney, Agent, or Firm* — MORRISON & FOERSTER LLP

(57) ABSTRACT

The present disclosure relates in some aspects to methods and compositions for analyzing a biological sample, comprising performing rolling circle amplification of a circRNA in situ in a biological sample, thereby generating an RCA product comprising multiple complementary copies of the circRNA and detecting the RCA product in situ at a spatially localized position in the biological sample.

19 Claims, 5 Drawing Sheets

(56) References Cited

U.S. PATENT DOCUMENTS 5,151,507 A 9/1992 Hobbs et al.
5,188,934 A 2/1993 Menchen et al.
5,192,782 A 3/1993 Djuric et al.
5,198,537 A 3/1993 Huber et al.
5,344,757 A 9/1994 Holtke et al.
5,354,657 A 10/1994 Holtke et al.
5,366,860 A 11/1994 Bergot et al.
5,512,462 A 4/1996 Cheng
5,599,675 A 2/1997 Brenner
5,635,352 A 6/1997 Urdea et al.
5,688,648 A 11/1997 Mathies et al.
5,695,940 A 12/1997 Drmanac et al.
5,702,888 A 12/1997 Holtke et al.
5,750,341 A 5/1998 Macevicz
5,800,996 A 9/1998 Lee et al.
5,847,162 A 12/1998 Lee et al.
5,990,479 A 11/1999 Weiss et al.
6,054,274 A 4/2000 Sampson et al.
6,172,218 B1 1/2001 Brenner
6,207,392 B1 3/2001 Weiss et al.
6,251,303 B1 6/2001 Bawendi et al.
6,291,187 B1 9/2001 Kingsmore et al.
6,306,597 B1 10/2001 Macevicz
6,319,426 B1 11/2001 Bawendi et al.
6,322,901 B1 11/2001 Bawendi et al.
6,323,009 B1 11/2001 Lasken et al.
6,344,329 B1 2/2002 Lizardi et al.
6,368,801 B1 4/2002 Faruqi
6,391,937 B1 5/2002 Beuhler et al.
6,423,551 B1 7/2002 Weiss et al.
6,426,513 B1 7/2002 Bawendi et al.
6,444,143 B2 9/2002 Bawendi et al.
6,534,266 B1 3/2003 Singer
6,576,291 B2 6/2003 Bawendi et al.
6,828,109 B2 12/2004 Kaplan
6,969,488 B2 11/2005 Bridgham et al.
7,057,026 B2 6/2006 Barnes et al.
7,255,994 B2 8/2007 Lao
7,345,159 B2 3/2008 Ju et al.
7,473,767 B2 1/2009 Dimitrov
7,534,991 B2 5/2009 Miller et al.
7,544,794 B1 6/2009 Benner
7,555,155 B2 6/2009 Levenson et al.
7,566,537 B2 7/2009 Balasubramanian et al.
7,632,641 B2 12/2009 Dirks et al.
7,655,898 B2 2/2010 Miller
7,721,721 B1 5/2010 Kronengold et al.
7,893,227 B2 2/2011 Wu et al.
7,910,304 B2 3/2011 Drmanac
7,941,279 B2 5/2011 Hwang et al.
7,989,166 B2 8/2011 Koch et al.
8,124,751 B2 2/2012 Pierce et al.
8,199,999 B2 6/2012 Hoyt et al.
8,268,554 B2 9/2012 Schallmeiner
8,330,087 B2 12/2012 Domenicali
8,415,102 B2 4/2013 Geiss et al.
8,431,691 B2 4/2013 McKernan et al.
8,460,865 B2 6/2013 Chee et al.
8,462,981 B2 6/2013 Determan et al.
8,481,258 B2 7/2013 Church et al.
8,519,115 B2 8/2013 Webster et al.
8,551,710 B2 10/2013 Bernitz et al.
8,632,975 B2 1/2014 Vander Horn et al.
8,658,361 B2 2/2014 Wu et al.
8,771,950 B2 7/2014 Church et al.
8,986,926 B2 3/2015 Ferree et al.
9,201,063 B2 12/2015 Sood et al.
9,217,178 B2 12/2015 Fedurco et al.
9,273,349 B2 3/2016 Nguyen et al.
9,371,563 B2 6/2016 Geiss et al.
9,371,598 B2 6/2016 Chee
9,376,717 B2 6/2016 Gao et al.
9,512,422 B2 12/2016 Barnard et al.
9,541,504 B2 1/2017 Hoyt
9,551,032 B2 1/2017 Landegren et al.
9,624,538 B2 4/2017 Church et al.
9,650,406 B2 5/2017 Zhou et al.
9,714,446 B2 7/2017 Webster et al.
9,714,937 B2 7/2017 Dunaway
9,727,810 B2 8/2017 Fodor et al.
9,778,155 B2 10/2017 Gradinaru et al.
9,783,841 B2 10/2017 Nolan et al.
9,889,422 B2 2/2018 Smith et al.
9,909,167 B2 3/2018 Samusik et al.
10,032,064 B2 7/2018 Hoyt
10,059,990 B2 8/2018 Boyden et al.
10,126,242 B2 11/2018 Miller et al.
10,138,509 B2 11/2018 Church et al.
10,179,932 B2 1/2019 Church et al.
10,227,639 B2 3/2019 Levner et al.
10,246,700 B2 4/2019 Dunaway et al.
10,266,888 B2 4/2019 Daugharthy et al.
10,267,808 B2 4/2019 Cai
10,309,879 B2 6/2019 Chen et al.
10,317,321 B2 6/2019 Tillberg et al.
10,364,457 B2 7/2019 Wassie et al.
10,370,698 B2 8/2019 Nolan et al.
10,415,080 B2 9/2019 Dunaway et al.
10,457,980 B2 10/2019 Cai et al.
10,465,235 B2 11/2019 Gullberg et al.
10,494,662 B2 12/2019 Church et al.
10,495,554 B2 12/2019 Deisseroth et al.
10,501,777 B2 12/2019 Beechem et al.
10,501,791 B2 12/2019 Church et al.
10,510,435 B2 12/2019 Cai et al.
10,526,649 B2 1/2020 Chen et al.
10,545,075 B2 1/2020 Deisseroth et al.
10,580,128 B2 3/2020 Miller
10,640,816 B2 5/2020 Beechem et al.
10,640,826 B2 5/2020 Church et al.
10,669,569 B2 6/2020 Gullberg et al.
10,746,981 B2 8/2020 Tomer et al.
10,774,372 B2 9/2020 Chee et al.
10,774,374 B2 9/2020 Frisén et al.
10,794,802 B2 10/2020 Gradinaru et al.
10,802,262 B2 10/2020 Tomer et al.
10,815,519 B2 10/2020 Husain et al.
10,829,814 B2 11/2020 Fan et al.
10,844,426 B2 11/2020 Daugharthy et al.
10,858,698 B2 12/2020 Church et al.
10,872,679 B2 12/2020 Cai et al.
10,964,001 B2 3/2021 Miller
11,174,281 B1 11/2021 Graham et al.
11,287,422 B2 3/2022 Previte et al.
11,434,525 B2 9/2022 Glezer
11,459,603 B2 10/2022 Tyagi et al.
11,499,185 B2 11/2022 Vijayan et al.
11,643,679 B2 5/2023 Glezer et al.
11,999,999 B2 6/2024 Ju et al.
2002/0045045 A1 4/2002 Adams et al.
2003/0017264 A1 1/2003 Treadway et al.
2005/0100900 A1 5/2005 Kawashima et al.
2006/0188901 A1 8/2006 Barnes et al.
2006/0234261 A1 10/2006 Pierce et al.
2006/0240439 A1 10/2006 Smith et al.
2006/0281109 A1 12/2006 Ost et al.
2007/0166705 A1 7/2007 Milton et al.
2009/0118128 A1 5/2009 Liu et al.
2010/0055733 A1 3/2010 Lutolf et al.
2011/0059865 A1 3/2011 Smith et al.
2011/0223585 A1 9/2011 Gullberg et al.
2012/0270305 A1 10/2012 Reed et al.
2013/0079232 A1 3/2013 Kain et al.
2013/0260372 A1 10/2013 Buermann et al.
2013/0288249 A1 10/2013 Gullberg et al.
2013/0323729 A1 12/2013 Landegren et al.
2016/0024555 A1 1/2016 Church et al.
2016/0108458 A1 4/2016 Frei et al.
2016/0305856 A1 10/2016 Boyden et al.
2016/0369329 A1 12/2016 Cai et al.
2016/0376642 A1 12/2016 Landegren et al.
2017/0009278 A1 1/2017 Söderberg et al.
2017/0081489 A1 3/2017 Rodriques et al.
2017/0101672 A1 4/2017 Luo et al.

(56) References Cited

U.S. PATENT DOCUMENTS

2017/0219465 A1 8/2017 Desseroth et al.
2017/0220733 A1 8/2017 Zhuang et al.
2017/0253918 A1 9/2017 Kohman
2018/0052081 A1 2/2018 Kohman
2018/0080876 A1 3/2018 Rockel et al.
2018/0208967 A1 7/2018 Larman et al.
2018/0237864 A1 8/2018 Imler et al.
2018/0251833 A1 9/2018 Daugharthy et al.
2018/0320226 A1 11/2018 Church et al.
2019/0017106 A1 1/2019 Frisen et al.
2019/0032128 A1 1/2019 Chen et al.
2019/0055594 A1 2/2019 Samusik et al.
2019/0106733 A1 4/2019 Kishi et al.
2019/0112599 A1 4/2019 Church et al.
2019/0119735 A1 4/2019 Deisseroth et al.
2019/0155835 A1 5/2019 Daugharthy et al.
2019/0161796 A1 5/2019 Hauling et al.
2019/0177718 A1 6/2019 Church et al.
2019/0194709 A1 6/2019 Church et al.
2019/0218608 A1 7/2019 Daugharthy et al.
2019/0249248 A1 8/2019 Beechem et al.
2019/0264270 A1 8/2019 Zhuang et al.
2019/0271028 A1 9/2019 Khafizov et al.
2019/0276881 A1 9/2019 Zhuang et al.
2019/0339203 A1 11/2019 Miller et al.
2019/0376956 A1 12/2019 Bobrow et al.
2020/0010891 A1 1/2020 Beechem et al.
2020/0071751 A1 3/2020 Daugharthy et al.
2020/0123597 A1 4/2020 Daniel
2020/0140920 A1 5/2020 Pierce et al.
2020/0224243 A1 7/2020 Desai et al.
2020/0224244 A1 7/2020 Nilsson et al.
2020/0239946 A1 7/2020 Dewal
2020/0354774 A1 11/2020 Church et al.
2020/0354782 A1 11/2020 Dewal
2020/0362398 A1 11/2020 Kishi et al.
2020/0393343 A1 12/2020 Kennedy-Darling et al.
2020/0399689 A1 12/2020 Luo et al.
2021/0017587 A1 1/2021 Cai et al.
2021/0115504 A1 4/2021 Cai et al.
2021/0164039 A1 6/2021 Wang et al.
2021/0222234 A1 7/2021 Carlson
2021/0238662 A1 8/2021 Bava et al.
2021/0238674 A1 8/2021 Bava
2021/0254140 A1 8/2021 Stahl et al.
2021/0262018 A1 8/2021 Bava et al.
2021/0277460 A1 9/2021 Bava
2021/0340621 A1 11/2021 Daugharthy et al.
2021/0388423 A1 12/2021 Bava et al.
2021/0388424 A1 12/2021 Bava
2022/0026433 A1 1/2022 Guo et al.
2022/0049302 A1 2/2022 Daugharthy et al.
2022/0049303 A1 2/2022 Busby et al.
2022/0064697 A1 3/2022 Zhuang et al.
2022/0083832 A1 3/2022 Shah
2022/0084628 A1 3/2022 Shah
2022/0084629 A1 3/2022 Shah
2022/0128565 A1 4/2022 Miller et al.
2022/0136049 A1 5/2022 Bava et al.
2022/0186300 A1 6/2022 Bava
2022/0195498 A1 6/2022 Kuhnemund et al.
2022/0213529 A1 7/2022 Kuhnemund et al.
2022/0228200 A1 7/2022 Bava
2022/0235403 A1 7/2022 Costa
2022/0282306 A1 9/2022 Bava et al.
2022/0282316 A1 9/2022 Bava
2022/0282319 A1 9/2022 Verheyen
2022/0372570 A1 11/2022 Costa
2022/0380838 A1 12/2022 Kuhnemund et al.
2022/0403458 A1 12/2022 Bava
2023/0002808 A1 1/2023 Mignardi
2023/0012607 A1 1/2023 Kuhnemund et al.
2023/0013775 A1 1/2023 Chen et al.
2023/0015226 A1 1/2023 Chen et al.
2023/0026886 A1 1/2023 Chen
2023/0031305 A1 2/2023 Hernandez Neuta et al.
2023/0031996 A1 2/2023 Hernandez Neuta et al.
2023/0035685 A1 2/2023 Hernandez Neuta et al.
2023/0037182 A1 2/2023 Bava et al.
2023/0039148 A1 2/2023 Verheyen
2023/0041485 A1 2/2023 Hernandez Neuta et al.
2023/0044650 A1 2/2023 Dockter
2023/0057571 A1 2/2023 Costa et al.
2023/0061542 A1 3/2023 Kuhnemund
2023/0084407 A1 3/2023 Hernandez Neuta et al.
2023/0159997 A1 5/2023 Belhocine et al.
2023/0160794 A1 5/2023 Dockter et al.
2023/0183787 A1 6/2023 Bava et al.
2023/0242974 A1 8/2023 Costa et al.
2023/0279465 A1 9/2023 He et al.
2023/0279475 A1 9/2023 Kuhnemund et al.
2023/0279480 A1 9/2023 Kuhnemund
2023/0287478 A1 9/2023 Bava
2023/0314327 A1 10/2023 Hoffman
2023/0314328 A1 10/2023 Costa
2023/0323427 A1 10/2023 Schnall-Levin
2023/0323430 A1 10/2023 Shastry
2023/0323437 A1 10/2023 Chen et al.
2023/0374573 A1 11/2023 Qian et al.
2023/0374580 A1 11/2023 Costa
2023/0416821 A1 12/2023 Bava et al.
2024/0002902 A1 1/2024 Jakobsen et al.
2024/0026426 A1 1/2024 Bava
2024/0026427 A1 1/2024 Kuhnemund et al.
2024/0026439 A1 1/2024 Sasaki
2024/0026448 A1 1/2024 Costa
2024/0035070 A1 2/2024 Christopherson
2024/0035071 A1 2/2024 Delaney et al.
2024/0035072 A1 2/2024 Christopherson
2024/0043910 A1 2/2024 Shastry
2024/0043914 A1 2/2024 Chen et al.
2024/0060119 A1 2/2024 Bava
2024/0084373 A1 3/2024 Shastry
2024/0084378 A1 3/2024 Marks et al.
2024/0101978 A1 3/2024 Boghospor et al.
2024/0132938 A1 4/2024 Kuhnemund
2024/0141418 A1 5/2024 Mielinis
2024/0150816 A1 5/2024 Feng et al.
2024/0158852 A1 5/2024 Belhocine et al.
2024/0167081 A1 5/2024 Bava et al.
2024/0175082 A1 5/2024 Costa
2024/0175083 A1 5/2024 Bava et al.
2024/0191297 A1 6/2024 Christopherson et al.
2024/0209330 A1 6/2024 Shastry et al.
2024/0218424 A1 7/2024 Costa et al.
2024/0218437 A1 7/2024 Belhocine et al.
2024/0263219 A1 8/2024 Kuhnemund
2024/0263220 A1 8/2024 Olofsson
2024/0264155 A1 8/2024 Costa

FOREIGN PATENT DOCUMENTS

WO WO 2019/199579 10/2019
WO WO 2020/076976 4/2020
WO WO 2020/076979 4/2020
WO WO 2020/096687 5/2020
WO WO 2020/099640 5/2020
WO WO 2020/117914 6/2020
WO WO 2020/123316 6/2020
WO WO 2020/123742 6/2020
WO WO 2020/142490 7/2020
WO WO 2020/240025 12/2020
WO WO 2020/254519 12/2020
WO WO 2021/123282 6/2021
WO WO 2021/123286 6/2021
WO WO 2021/138676 7/2021
WO WO 2021/155063 8/2021
WO WO 2021/168326 8/2021
WO WO 2023/108139 6/2023
WO WO 2023/141476 7/2023
WO WO 2023/172915 9/2023

(56) References Cited

FOREIGN PATENT DOCUMENTS

WO WO 2023/192302 10/2023
WO WO 2024/148300 7/2024

OTHER PUBLICATIONS

Baner et al., "Signal amplification of padlock probes by rolling circle replication," Nucleic Acids Res. (1998) 26(22):5073-5078.
Bibikova et al., "Quantitative gene expression profiling in formalin-fixed, paraffin-embedded tissues using universal bead arrays," Am J Pathol. Nov. 2004; 165(5):1799-807.
Bolognesi et al., "Multiplex Staining by Sequential Immunostaining and Antibody Removal on Routine Tissue Sections," J. Histochem. Cytochem. (2017); 65(8):431-444.
Capodieci et al., "Gene expression profiling in single cells within tissue," Nat Methods. (2005) 2(9): 663-5.
Chen et al., "Nanoscale imaging of RNA with expansion microscopy," Nat Methods. (2016) 13:679-684.
Chen et al., "RNA imaging. Spatially resolved, highly multiplexed RNA profiling in single cells," Science. (2015) 348(6233): aaa6090. 16 pgs.
Chen et al., "Expansion Microscopy," Science (2015) 347(6221):543-548.
Choi et al., "Programmable in situ amplification for multiplexed imaging of mRNA expression," Nat Biotechnol. (2010) 28(11): 1208-1212.
Conze et al., "Single molecule analysis of combinatorial splicing," Nucleic Acids Res. (2010) 38(16): e163.
Dean et al., "Rapid Amplification Of Plasmid And Phage DNA Using Phi29 DNA Polymerase And Multiply-Primed Rolling Circle Amplification," Genome Research (2001) 11:1095-1099.
Dirks et al., "Triggered amplification by hybridization chain reaction," Proc Natl Acad Sci U S A. (2004) 101(43): 15275-15278.
Eng et al., "Transcriptome-scale super-resolved imaging in tissues by RNA seqFISH," Nature. (2019) 568(7751): 235-239.
Faruqi et al., "High-throughput genotyping of single nucleotide polymorphisms with rolling circle amplification," BMC Genomics. (2001) 2:4.
Femino et al., "Visualization of single RNA transcripts in situ," Science. (1998) 280(5363): 585-90.
Forcucci et al., "All-plastic miniature fluorescence microscope for point-of-care readout of bead-based bioassays," J Biomed Opt. (2015) 20(10): 105010.
Gavrilovic et al., "Automated classification of multicolored rolling circle products in dual-channel wide-field fluorescence microscopy," Cytometry A. (2011) 79(7): 518-27.
Geiss et al., "Direct multiplexed measurement of gene expression with color-coded probe pairs," Nat Biotechnol. (2008) 26(3): 317-25.
Glass et al., "SIMPLE: a sequential immunoperoxidase labeling and erasing method," J Histochem Cytochem. (2009) 57(10); 899-905.
Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.
Goransson et al., "A single molecule array for digital targeted molecular analyses," Nucleic Acids Res. 2009 37(1): e7. doi: 10.1093/nar/gkn921.
Gunderson et al. "Decoding randomly ordered DNA arrays." Genomne research 14.5 (2004): 870-877.
Gyllborg et al., "Hybridization-based in situ sequencing (HybISS) for spatially resolved transcriptomics in human and mouse brain tissue," Nucleic Acids Res. (2020) 48(19): e112.
Han et al., "Quantum-dot-tagged microbeads for multiplexed optical coding of biomolecules," Nat Biotechnol. (2001) 19(7): 631-5.
Henegariu et al., "Custom fluorescent-nucleotide synthesis as an alternative method for nucleic acid labeling," Nature Biotechnol. (2000) 18:345.
Itzkovitz et al., "Single-molecule transcript counting of stem-cell markers in the mouse intestine," Nat Cell Biol. (2011) 14(1): 106-14.
Itzkovitz et al., "Validating Transcripts with Probes and Imaging Technology," Nat Methods. (2011) 8(4 Suppl): S12-S19.
Jamur et al., "Permeabilization of cell membranes," Method Mol. Biol. (2010) 588: 63-66 (abstract only).
Korlach et al. "Selective aluminum passivation for targeted immobilization of single DNA polymerase molecules in zero-mode waveguide nanostructures." *Proceedings of the National Academy of Sciences* 105.4 (2008): 1176-1181.
Lagunavicius et al., "Novel application of Phi29 DNA polymerase: RNA detection and analysis in vitro and in situ by target RNA-primed RCA," RNA. (2009) 15(5):765-71.
Lakowicz et al., "Silver particles enhance emission of fluorescent DNA oligomers," Bio Techniques (2003) 34(1); 62-66.
Larsson et al. "In situ detection and genotyping of individual mRNA molecules," Nat Methods. (2010) 7(5):395-397.
Lee et al. "Highly Multiplexed Subcellular RNA Sequencing In Situ", Science (2014) 343(6177):1360-1363.
Levene et al. "Zero-mode waveguides for single-molecule analysis at high concentrations." *science* 299.5607 (2003): 682-686.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Lin et al., "Highly multiplexed imaging of single cells using a high-throughput cyclic immunofluorescence method," Nat Commun. (2015) 6:8390.
Liu et al. Barcoded oligonucleotides ligated on RNA amplified for multiplexed and parallel in situ analyses. Nucleic Acids Res. (2021) 49(10): e58, 15 pages. doi: 10.1093/nar/gkab120.
Liu et al., "Direct detection of circRNA in real samples using reverse transcription—rolling circle amplification," Anal Chim Acta. (2020) 1101:169-175.
Lizardi et al., "Mutation detection and single-molecule counting using isothermal rolling-circle amplification," Nat Genet. (1998) 19(3): 225-232.
Lundquist et al. "Parallel confocal detection of single molecules in real time." Optics letters 33.9 (2008): 1026-1028.
Maierhorfer et al., "Multicolor deconvolution microscopy of thick biological specimens," Am J Pathol. (2003) 162(2): 373-9.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Mitra et al., "Fluorescent in situ sequencing on polymerase colonies," Anal. Biochem. (2003) 320, 55-65.
Mohsen et al., "The Discovery of Rolling Circle Amplification and Rolling Circle Transcription," Acc Chem Res. (2016) 49(11): 2540-2550.
Nallur et al., "Signal amplification by rolling circle amplification on DNA microarrays," Nucleic Acids Res. (2001) 29(23): e118.
Niu et al., "Fluorescence detection for DNA using hybridization chain reaction with enzyme-amplification," Chem C+A277ommun (Camb). (2010) 46(18): 3089-91.
Payne et al. "In situ genome sequencing resolves DNA sequence and structure in intact biological samples," Science. (2021) 371(6532): eaay3446. doi: 10.1126/science.aay3446. Epub Dec. 31, 2020.
Pirici et al., "Antibody elution method for multiple immunohistochemistry on primary antibodies raised in the same species and of the same subtype," J Histochem Cytochem. (2009) 57(6); 567-75.
Raj et al., "Imaging individual mRNA molecules using multiple singly labeled probes," Nat Methods. (2008) 5(10): 877-879.
Rajeswari et al., "Multiple pathogen biomarker detection using an encoded bead array in droplet PCR," J Microbiol Methods. (2017) 139: 22-28.
Rouhanifard et al. "ClampFISH detects individual nucleic acid molecules using click chemistry-based amplification," Nat Biotechnol. (2018) 17 pages. doi: 10.1038/nbt.4286.

(56) References Cited

OTHER PUBLICATIONS

Schweitzer et al. "Immunoassays with rolling circle DNA amplification: A versatile platform for ultrasensitive antigen detection," Proc. Natl Acad. Sci. USA (2000) 97:10113-119.
Schweitzer et al., "Multiplexed protein profiling on microarrays by rolling-circle amplification," Nature Biotech. (2002) 20:359-365.
Shendure et al, "Accurate multiplex polony sequencing of an evolved bacterial genome," Science (2005) 309(5741); 1728-1732.
Song et al., "Hybridization chain reaction-based aptameric system for the highly selective and sensitive detection of protein," Analyst. (2012) 137(6):1396-1401.
Sun et al., "Composite organic-inorganic nanoparticles as Raman labels for tissue analysis," Nano Lett. (2007) 7(2): 351-6.
Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.
Wählby et al., "Sequential immunofluorescence staining and image analysis for detection of large numbers of antigens in individual cell nuclei," Cytometry. (2002) 47(1): 32-41.
Weibrecht et al., "Simultaneous visualization of both signaling cascade activity and end-point gene expression in single cells," PLoS One. (2011) 6(5): e20148.
Wetmur, "DNA Probes: Applications of the Principles of Nucleic Acid Hybridization," Critical Reviews in Biochemistry and Molecular Biology, (1991) 26(91); 227-259.
Wilson et al., "Encoded microcarriers for high-throughput multiplexed detection," Angew Chem Int Ed Engl. (2006) 18;45(37): 6104-17.
Wu, C. et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.
Xia et al. "Multiplexed detection of RNA using MERFISH and branched DNA amplification." Scientific reports 9.1 (2019): 1-13.
Zhao et al., "Advances of multiplex and high throughput biomolecular detection technologies based on encoding microparticles," Sci China Chem. (2011) 54(8):1185.
Chemeris et al., "Real-time hybridization chain reaction," Dokl Biochem Biophys. (2008) 419: 53-55.
Chen et al., "Efficient in situ barcode sequencing using padlock probe-based BaristaSeq," Nucleic Acids Res. (2018) 46(4): e22.
Sun et al., "Integrating barcoded neuroanatomy with spatial transcriptional profiling enables identification of gene correlates of projections," Nat Neurosci. (2021) 24(6):873-885.

* cited by examiner

METHOD OF IDENTIFYING CIRCULAR RNA

CROSS-REFERENCE TO RELATED APPLICATIONS

This application claims priority to U.S. Provisional Patent Application No. 63/343,922, filed May 19, 2022, entitled "METHOD OF IDENTIFYING CIRCULAR RNA," which is herein incorporated by reference in its entirety for all purposes.

FIELD

The present disclosure relates in some aspects to methods for identifying circular RNA, including the spatial identification of circular RNA in situ.

BACKGROUND

Improved methods for identifying circular RNA, including the spatial identification of circular RNA in situ, are needed. Provided herein are methods and compositions that address such and other needs.

SUMMARY

In some aspects, provided herein is a method for analyzing a biological sample, comprising: contacting the biological sample with a primer, wherein the primer hybridizes to a target sequence in a target circular RNA (circRNA); using a reverse transcriptase to perform rolling circle amplification (RCA) of the circRNA, thereby generating an RCA product comprising multiple complementary copies of the circRNA; and detecting the RCA product in situ at a spatially localized position in the biological sample.

In some embodiments, the method comprises performing an RNase digestion in the sample prior to RCA using an RNase. In some embodiments, the RNase digestion enriches for circRNA in the sample. In any of the preceding embodiments, the RNase digestion comprises digesting linear RNA in the sample. In any of the preceding embodiments, the method comprises contacting the sample with an RNase for digesting linear RNA in the sample. In any of the preceding embodiments, the RNase is an exonuclease. In any of the preceding embodiments, the RNase is RNase R. In any of the preceding embodiments, the method does not comprise enriching for circRNA in the sample prior to performing RCA.

In any of the preceding embodiments, the reverse transcriptase can be a DNA strand-displacing reverse transcriptase. In any of the preceding embodiments, the reverse transcriptase can lack RNase H activity. In any of the preceding embodiments, the reverse transcriptase can be a Murine Leukemia Virus reverse transcriptase (MuLV RT) or a derivative thereof. In any of the preceding embodiments, the reverse transcriptase is a Moloney-murine leukemia virus reverse transcriptase (M-MuLV RT) or a derivative thereof.

In any of the preceding embodiments, the target sequence can comprise a splice junction in the circRNA. In some embodiments, the splice junction is a back-splice junction. In some embodiments, the back-splice junction is generated by back-splicing, wherein back-splicing comprises splicing of a pre-mRNA wherein a downstream 5' splice site is joined to an upstream 3' splice site, thereby generating a circRNA.

In any of the preceding embodiments, the target sequence can be a sequence that is not present in linear RNA.

In any of the preceding embodiments, the circRNA and/or RCA product can comprise one or more marker sequences. In some embodiments, one or more of the marker sequences comprise a splice junction present in the circRNA, or a complement thereof present in the RCA product. In any of the preceding embodiments, the circRNA and/or RCA product comprise multiple marker sequences, wherein the combination of the marker sequences identifies the circRNA, and wherein detecting the RCA product comprises detecting the combination of the marker sequences.

In any of the preceding embodiments, the multiple marker sequences are multiple splice junctions present in the circRNA. In some embodiments, the multiple splice junctions comprise a back-splice junction. In any of the preceding embodiments, the one or more marker sequences identify an isoform of the circRNA. In any of the preceding embodiments, the one or more marker sequences are independently between about 5 and about 40 nucleotides in length.

In some embodiments, also provided is a method for analyzing a biological sample, comprising: digesting linear RNA in the sample using RNase R; contacting the biological sample with a primer, wherein the primer hybridizes to a target sequence in a target circular RNA (circRNA), wherein the target sequence comprises a back-splice junction; using a reverse transcriptase having strand displacing activity to perform rolling circle amplification (RCA) of the circRNA, thereby generating an RCA product comprising multiple complementary copies of the circRNA in the biological sample; and detecting the RCA product in situ at a spatially localized position in the biological sample, wherein detecting the RCA product comprises detecting one or more marker sequences comprising a complement of a splice junction present in the circRNA.

In some embodiments, the reverse transcriptase lacks RNase activity. In any of the preceding embodiments, the reverse transcriptase is a Murine Leukemia Virus reverse transcriptase (MuLV RT) or a derivative thereof. In any of the preceding embodiments, the reverse transcriptase is a Moloney-murine leukemia virus reverse transcriptase (M-MuLV RT) or a derivative thereof.

In any of the preceding embodiments, detecting the RCA product comprises contacting the biological sample with one or more detectably-labeled probes that directly or indirectly hybridize to the RCA product. In some embodiments, detecting the RCA product comprises contacting the biological sample with one or more detectably-labeled probes that directly or indirectly hybridize to the one or more marker sequences comprised by the RCA product. In some embodiments, detecting the RCA product comprises detecting a signal associated with the one or more detectably-labeled probes.

In some of any such embodiments, the signal associated with the one or more detectably-labeled probes is amplified in situ in the biological sample. In some embodiments, the signal amplification comprises rolling circle amplification (RCA) of a probe that directly or indirectly binds to the RCA product; hybridization chain reaction (HCR) directly or indirectly on the RCA product; linear oligonucleotide hybridization chain reaction (LO-HCR) directly or indirectly on the RCA product; primer exchange reaction (PER) directly or indirectly on the RCA product; assembly of branched structures directly or indirectly on the RCA product; hybridization of a plurality of detectable probes directly or indirectly on the RCA product, or any combination thereof.

In any of the preceding embodiments, detecting the RCA product comprises sequencing all or a portion of the RCA product and/or in situ hybridization to the RCA product. In some embodiments, detecting the RCA product comprises sequencing the one or more marker sequences in the RCA product and/or in situ hybridization to the one or more marker sequences in the RCA product. In any of the preceding embodiments, the sequencing comprises sequencing by hybridization, sequencing by ligation, and/or fluorescent in situ sequencing. In any of the preceding embodiments, the in situ hybridization comprises sequential fluorescent in situ hybridization.

In any of the preceding embodiments, the biological sample is non-homogenized. In any of the preceding embodiments, the biological sample is selected from the group consisting of a formalin-fixed, paraffin-embedded (FFPE) sample; a frozen tissue sample; and a fresh tissue sample. In any of the preceding embodiments, the biological sample is fixed. In any of the preceding embodiments, the biological sample is not fixed. In any of the preceding embodiments, the biological sample is permeabilized. In any of the preceding embodiments, the biological sample is embedded in a matrix. In any of the preceding embodiments, the matrix comprises a hydrogel. In any of the preceding embodiments, the biological sample is cleared. In any of the preceding embodiments, the clearing comprises contacting the biological sample with a proteinase. In any of the preceding embodiments, the biological sample is cross-linked. In any of the preceding embodiments, the biological sample is a tissue slice between about 1 μm and about 50 μm in thickness. In any of the preceding embodiments, the tissue slice is between about 5 μm and about 35 μm in thickness.

BRIEF DESCRIPTION OF THE DRAWINGS

The drawings illustrate certain features and advantages of this disclosure. These embodiments are not intended to limit the scope of the appended claims in any manner.

FIG. 2A depicts an exemplary circRNA having four splice junctions that can be used as barcodes, which includes the splice junction linking Exon 3 and Exon 6 (splice junction 1), the splice junction linking Exon 6 and Exon 7 (splice junction 2), the splice junction linking Exon 7 and Exon 9 (splice junction 3), and the splice junction linking Exon 9 and Exon 3 (splice junction 4). In FIG. 2A, splice junction 4 is also depicted as the back-splice junction. FIG. 2B depicts an exemplary circRNA having three splice junctions, where each of the three splice junctions comprises a marker sequence, which can be used as a barcode. In FIG. 2B, there is a marker sequence at splice junction 1 (linking Exon 1 and Exon 2), there is a marker sequence at splice junction 2 (linking Exon 2 and Exon 3), and there is a marker sequence at splice junction 3 (linking Exon 3 and Exon 1). In FIG. 2B, splice junction 3 is also depicted as the back-splice junction.

FIG. 3A depicts the targeting of a circRNA using a primer that hybridizes to a marker sequence that comprises the back-splice junction of the circRNA. FIG. 3B depicts the RCA of the exemplary circRNA using a strand displacing reverse transcriptase, which synthesizes multiple copies of the circRNA in a single linear RCA product.

DETAILED DESCRIPTION

Figure 1:
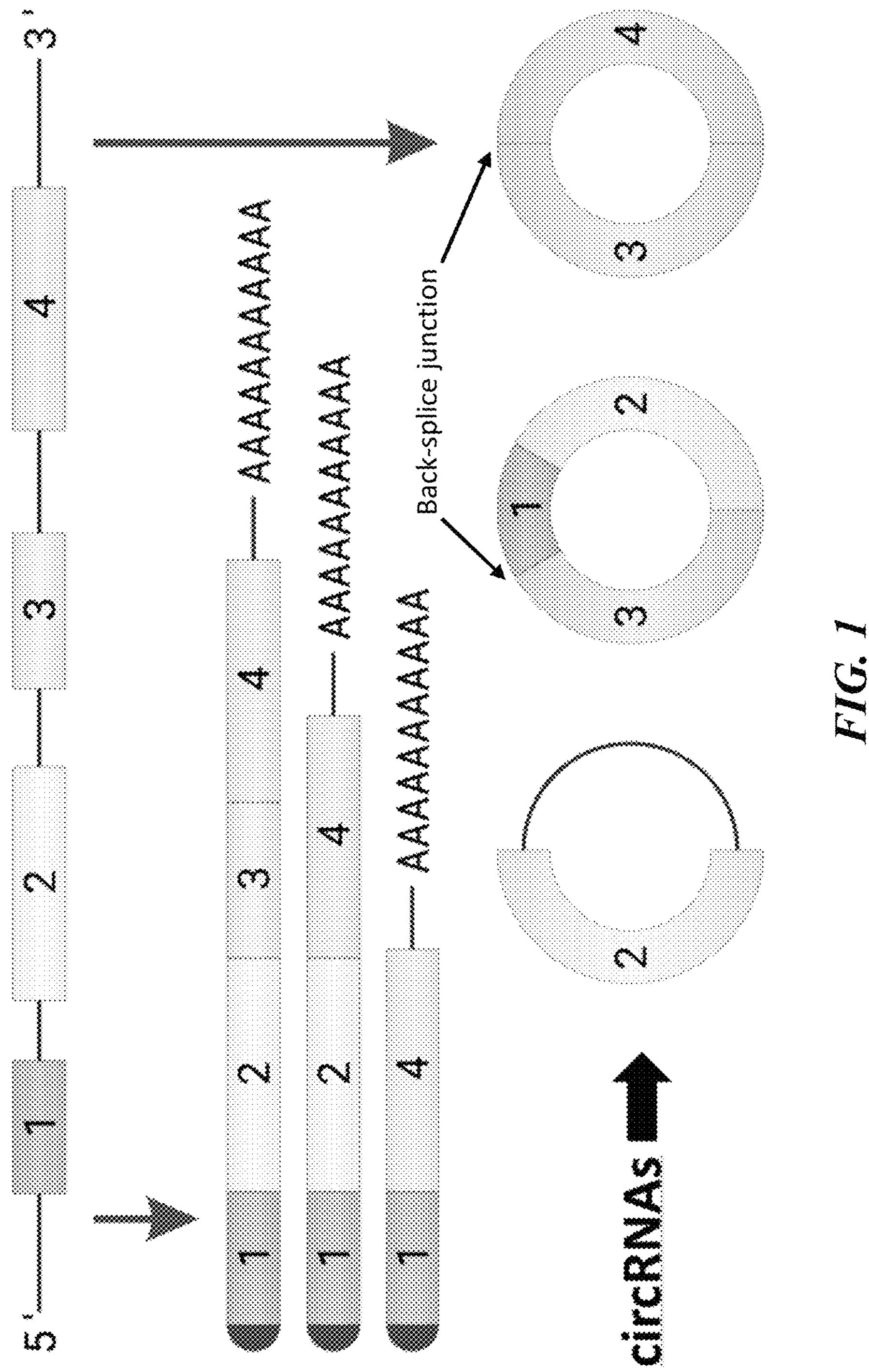
FIG. 1 depicts a schematic representation of an exemplary gene that includes exons 1, 2, 3, and 4, and its transcription to three different linear mRNA transcripts that differ as a result of pre-mRNA splicing, and three different circular RNA (cirRNA) transcripts that also differ as a result of pre-mRNA splicing that includes back-splicing at the back-splice junction.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Recently, circular RNAs (circRNAs) have emerged as an interesting class of biomolecule whose functional importance is beginning to be recognized and investigated. Methods for detecting circRNA in situ would be particularly beneficial for investigating the functional importance of circRNAs in biological samples, as well as for investigating the relevance of circRNAs for uses such as diagnosis and prognosis of a disease or disorder. In circRNA, the 3' and 5' ends that would normally be present in an mRNA molecule have been joined together in a reaction (e.g., a "back-splicing" event). The resulting RNA structure as a circRNA confers unique properties. For instance, circRNAs can be predominantly found in the cytoplasm, and the lack of a 5' cap and a 3' tail can make these circular molecules fairly resistant to RNase degradation as compared to their linear cognates. This results in a much longer half-life for circRNAs, which can be more than 24 hours due to the lack of a 5' cap and a 3' tail, as compared to linear RNAs that typically have a half-life of less than 30 minutes. Many circRNAs are present at low or very low levels compared to their linear counterparts, thereby being highly susceptible to molecule crowding by the abundance of linear RNA in the sample. This molecular crowding is a common obstacle when performing in situ analysis. Accordingly, the methods described herein for identifying circRNAs, including the spatial identification of circRNAs in situ, can advantageously be utilized for various purposes, including examining the functional importance, localization, expression, and presence of circRNAs in situ. The present disclosure provides methods and compositions for analysis of circRNAs in situ comprising performing rolling circle amplification of the circRNAs in situ in a sample.

In some aspects, provided herein is a method for analyzing a biological sample, comprising (a) contacting the biological sample with a primer, wherein the primer hybridizes to a target sequence in a target circular RNA (circRNA); (b) using a reverse transcriptase to perform rolling circle amplification (RCA) of the circRNA, thereby generating an RCA product comprising multiple complementary copies of the circRNA; and (c) detecting the RCA product in situ at a spatially localized position in the biological sample.

Also provided herein is a method for analyzing a biological sample, comprising (a) digesting linear RNA in the sample using RNase R; (b) contacting the biological sample with a primer, wherein the primer hybridizes to a target sequence in a target circular RNA (circRNA), wherein the target sequence comprises a back-splice junction; (c) using a reverse transcriptase having strand displacing activity to perform rolling circle amplification (RCA) of the circRNA, thereby generating an RCA product comprising multiple complementary copies of the circRNA in the biological sample; and (d) detecting the RCA product in situ at a spatially localized position in the biological sample, wherein detecting the RCA product comprises detecting one or more marker sequences comprising a complement of a splice junction present in the circRNA.

II. Circular RNAs, Primers, and Amplification

Provided herein are methods that may be used for the identification of circRNAs of interest, for example, for the spatial identification of a circRNA of interest in situ in a sample of interest. The methods and compositions disclosed herein can be used to detect and analyze a wide variety of different circRNAs. In some aspects, the methods and compositions disclosed herein can be used to detect and analyze any circRNA.

In some instances, the methods disclosed herein, e.g., methods for analyzing a biological sample, comprise (a) contacting a biological sample with a primer, wherein the primer hybridizes to a target sequence in a target circRNA; (b) using a reverse transcriptase to perform rolling circle amplification (RCA) of the circRNA, thereby generating an RCA product comprising multiple complementary copies of the circRNA; and (c) detecting the RCA product in situ at a spatially localized position in the biological sample.

In some instances, the methods disclosed herein, e.g., methods for analyzing a biological sample, comprise (a) digesting linear RNA in the sample using RNase R; (b) contacting the biological sample with a primer, wherein the primer hybridizes to a target sequence in a target circular RNA (circRNA), wherein the target sequence comprises a back-splice junction; (c) using a reverse transcriptase having strand displacing activity to perform rolling circle amplification (RCA) of the circRNA, thereby generating an RCA product comprising multiple complementary copies of the circRNA in the biological sample; and (d) detecting the RCA product in situ at a spatially localized position in the biological sample, wherein detecting the RCA product comprises detecting one or more marker sequences comprising a complement of a splice junction present in the circRNA.

A. Circular RNAs

In some instances, the target circRNA can be any circRNA, e.g., any circRNA that is present in a biological sample. In some instances, the target circRNA is a circular form of any linear RNA, wherein the circular form is created by linking the 5' and 3' ends of the linear RNA. As such, in some embodiments, the target circRNA can be a circRNA transcribed from any gene, e.g., any gene of interest. In some embodiments, the circRNA is selected from the group consisting of circHECTD1, circARHGAP10, has_circRNA 103809, has_circ_0017639, circSAMD4A, circPVT1, circTTN, circRHOT1, circEIF3J, circPAIP2, CDR1as (ciRS-7), circFAT1, circTADA2A, circITCH, circDLGAP4, circRHOBTB3, circCCDC9, circFAM114A2, circZNF532, circERBB2, circRHOT1, circSamd4, circSHKBP1, circAR3, circPLEKHM3, circSlc45a4, circCACNA2D1, circCACNA1E, circular sisRNAs, CDR1as (ciRS-7), circPANs, circK7.3s, circBHLF1, and tricRNAs. In some embodiments, the circRNA is an isoform of the circRNA. In some embodiments, the circRNA is an isoform of a circRNA transcribed from a gene, e.g., a gene of interest. In some embodiments, the circRNA is an endogenous circRNA.

In some instances, the target circRNA comprises a target sequence that the primer hybridizes to. In some embodiments, the target sequence comprises a splice junction in the circRNA. In some embodiments, the splice junction is a back-splice junction. A back-splice junction is, in some instances, generated by a downstream 5' splice site joining to an upstream 3' splice site, with the back-splice junction being the site where the downstream 5' splice site is linked to the upstream, 3' splice site. Accordingly, a back-splice junction is unique to circular RNAs since it is not present in the linear counterparts of the circRNAs. In some instances, the back-splice junction is generated by back-splicing.

In some instances, the back-splicing comprises splicing of a pre-mRNA, wherein a downstream 5' splice site is joined to an upstream 3' splice site, thereby generating a circRNA. In some embodiments, the target sequence is a sequence that is not present in linear RNA. In some embodiments, the splice junction is not present in linear RNA.

In some embodiments, the circRNA and/or the RCA product comprises one or more marker sequences. Each of the one or more marker sequences can be a sequence of the circRNA that identifies the circRNA individually or in combination with one or more other marker sequences. In some instances, one or more of the one or more marker sequences comprise a splice junction present in the circRNA, or a complement thereof present in the RCA product. In some instances, the circRNA and/or the RCA product comprises multiple marker sequences, wherein the combination of the marker sequences identifies the circRNA, and wherein detecting the RCA product comprises detecting the combination of the marker sequences.

In some instances, the multiple marker sequences are multiple splice junctions present in the circRNA. The number of splice junctions in the multiple splice junctions is not limited and may vary depending on the circRNA and the splicing of its pre-mRNA. In some embodiments, the multiple splice junctions comprise at least one, two, three, four, five, six, seven, eight, nine, or ten or more splice junctions. In some instances, the multiple splice junctions comprises one, two, three, four, or five splice junctions. Each of the multiple splice junctions can, in some instances, be any splice junction generated by pre-mRNA splicing, which can include a back-splice junction. Accordingly, in some embodiments, the multiple splice junctions comprise a back-splice junction. In some instances, the one or more marker sequences identify an isoform of the circRNA. For instance, due to different splicing that may occur to a pre-mRNA, multiple different isoforms of a circRNA derived from the same gene may be generated, which may differ with regards to, e.g., which exons are present and how they are spliced together. As such, different isoforms of a circRNA may contain different splice junctions as a result of having been generated by different splicing.

In some instances, the one or more marker sequences are independently between about 5 and about 60, about 5 and about 50, about 5 and about 40, about 5 and about 35, about 5 and about 30, about 5 and about 25, about 5 and about 20, about 10 and about 60, about 10 and about 50, about 10 and about 40, about 10 and about 35, about 10 and about 30, about 10 and about 25, about 10 and about 20, about 15 and about 60, about 15 and about 50, about 15 and about 40, about 15 and about 35, about 15 and about 30, about 15 and about 25, or about 15 and about 20 nucleotides in length. In some instances, the one or more marker sequences are independently 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some embodiments, the one or more marker sequences are independently between about 5 and about 40 nucleotides in length. In some embodiments, the one or more marker sequences are independently between about 10 and about 30 nucleotides in length. In some embodiments, the one or more marker sequences are independently between about 15 and about 20 nucleotides in length.

B. Enrichment of CircRNAs

In some embodiments, the method comprises enriching for circRNA in the sample prior to RCA using an RNase.

In some instances, the method comprises performing an RNase digestion in the sample prior to RCA using an RNase. In some embodiments, the method comprises contacting the sample with an RNase for digesting linear RNA in the sample. In some embodiments, the method comprises digesting linear RNA in the sample using an RNase, such as RNase R. Performing an RNase digestion in the sample prior to RCA, or contacting the sample with an RNase for digesting linear RNA, can promote the enrichment of circRNA in the sample by facilitating the degradation of linear RNA, for instance, that is present in the sample. Performing an RNase digestion can be highly advantageous because many circRNAs are present at low or very low levels compared to their linear counterparts, thereby being highly susceptible to molecule crowding by linear RNA in the sample, which is a common obstacle when performing in situ analysis. Thus, performing an RNase digestion as part of this method can greatly improve detection of circRNAs while also reducing background noise, which is especially important when performing an in situ assay, such as those as described herein.

In some instances, the contacting the sample with an RNase for digesting linear RNA in the sample, e.g., an exonuclease, such as RNase R, occurs prior to, simultaneously with, or after the sample is contacted with the primer and/or the RCA is performed. In some embodiments, the contacting the sample with an RNase for digesting linear RNA in the sample occurs prior to the sample being contacted with the primer and/or prior to performing the RCA.

Accordingly, in some instances, the RNase digestion enriches for circRNA in the sample. In some embodiments, the RNase digestion comprises digesting linear RNA in the sample. In some instances, the RNase is an exonuclease, e.g., an exoribonuclease, such as RNase R. In some embodiments, the RNase is RNase R.

In some embodiments, the method does not comprise enriching for circRNA in the sample prior to performing RCA, or does not comprise contacting the sample with an RNase for digesting linear RNA in the sample.

C. Primers

In some aspects, the method comprises contacting a biological sample with a primer, wherein the primer hybridizes to a target sequence in a target circRNA.

A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, in some cases, can be a primer binding sequence. A primer extension reaction is generally any method where two nucleic acid sequences become linked (e.g., hybridized) by an overlap of their respective terminal complementary nucleic acid sequences (e.g., 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, the primer hybridizes to a target sequence comprising a splice junction in the circRNA. The use of a primer that hybridizes to a target sequence comprising a splice junction in the circRNA is a form of barcoding because it is specific to a circRNA comprising that specific splice junction, such as a back-splice junction. Accordingly, a splice junction as described herein comprises a barcode. The barcode can be decoded using any of the various detection methods described herein, e.g., in Section III. In some embodiments, the primer hybridizes to a target sequence comprising a back-splice junction. Thus, in some embodiments, the method comprises contacting a biological sample with a primer, wherein the primer hybridizes to a target sequence in a target circRNA, and wherein the target sequence comprises a back-splice junction. In some instances, the primer hybridizes to nucleotides in the target sequence that flank or span both sides of the splice junction, e.g., the back-splice junction.

By hybridizing to a splice junction, e.g., a back-splice junction, the primer can result in amplification, e.g., rolling circle amplification, of a circRNA that comprises that specific splice junction (or barcode) generated as a result of pre-mRNA splicing. This includes back-splice junctions that are created by back-splicing of pre-mRNA, wherein a downstream 5' splice site is joined to an upstream 3' splice site, thereby generating a circRNA that comprises a back-splice junction. Such a back-splice junction would not be present in a linear RNA counterpart and, thus, amplification of a linear RNA counterpart would not be expected to occur if using a primer that hybridizes to the back-splice junction since the linear RCA counterpart would not comprise the sequence of the back-splice junction.

D. Rolling Circle Amplification

In some aspects, the method comprises using a reverse transcriptase to perform rolling circle amplification (RCA) of the circRNA.

In some embodiments, a product, e.g., RCA product, is a primer extension product of a circRNA, which can be generated using a primer as described above.

In some aspects, the method comprises using a reverse transcriptase to perform RCA of the circRNA, thereby generating an RCA product comprising multiple complementary copies of the circRNA. In some embodiments, the reverse transcriptase is a DNA strand-displacing reverse transcriptase. In some embodiments, the reverse transcriptase is engineered to have reduced RNase H activity compared to a wild-type reverse transcriptase. In some aspects, the reverse transcriptase lacks RNase H activity, e.g., is an RNase H minus reverse transcriptase. A reverse transcriptase that lacks RNase H activity avoids digesting the RNA template. In some embodiments, the reverse transcriptase is selected from the group consisting of Murine Leukemia Virus reverse transcriptase (MuLV RT), Moloney-Murine Leukemia Virus reverse transcriptase (M-MuLV RT), Maxima™ RNase H-minus reverse transcriptase, HiScript® III reverse transcriptase, ProtoScript® II reverse transcriptase, RevertAid™ H minus reverse transcriptase, and AMV reverse transcriptase. In some embodiments, the reverse transcriptase is a Murine Leukemia Virus reverse transcriptase (MuLV RT) or a derivative thereof. In some instances, the reverse transcriptase is a Moloney-Murine Leukemia Virus reverse transcriptase (M-MuLV RT) or a derivative thereof.

In some embodiments, a product of a circRNA, e.g., an RCA product, is generated by amplification using a primer that hybridizes to the circRNA. In some embodiments, the amplifying is achieved by performing rolling circle amplification (RCA) of the circRNA in situ, thereby generating an RCA product. In some instances, the RCA product is a linear RCA product. In some embodiments, the amplifying generates multiple copies of an RCA product from the circRNA. In some instances, the RCA product comprises multiple complementary copies of the circRNA. In some embodiments, amplifying comprises a single amplification step. In some instances, the amplifying comprises linear RCA amplification using the primer that hybridizes to the circRNA, thereby generating multiple complementary DNA copies of the circRNA. In some embodiments, the amplifying does not comprise a nested polymerase chain (nested PCR) reaction on the RCA product, or does not further comprise nested PCR of the RCA product. Accordingly, in some instances, the amplifying does not comprise two amplification steps, e.g., a cDNA synthesis step and a nested PCR amplification step. In some embodiments, the RCA comprises a linear RCA approach in situ. In some instances, the RCA does not comprise a nested primer (branched) RCA approach. In some embodiments, the RCA is a branched RCA. In a branched RCA approach, the initially formed cDNA for the RCA product is subsequently amplified by a set of primers specific for that RCA product.

In some embodiments, the RCA amplification in situ in the biological sample produces at least 10, at least 20, at least 30, at least 40, at least 50, at least 60, at least 100, or at least 200 complementary copies of the circRNA. In some instances, the RCA amplification in situ in the biological sample produces between about 30 and about 500, between about 30 and about 400, between about 30 and about 300, between about 30 and about 200, between about 30 and about 100, between about 30 and about 80, between about 30 and about 50, between about 50 and about 200, between about 50 and about 100, between about 50 and about 80, or between about 20 and about 100 complementary copies of the circRNA. In some embodiments, the RCA amplification in situ in the biological sample produces no more than about 200, no more than about 100, no more than about 80, no more than about 50, no more than about 40, or no more than about 30 complementary copies of the circRNA.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a reverse transcriptase, e.g., a DNA strand-displacing reverse transcriptase, in the presence of appropriate dNTP precursors and other cofactors, a primer is elongated to produce multiple complementary copies of the circRNA. This amplification step can utilize isothermal amplification or non-isothermal amplification. In some embodiments, after the formation of the hybridization complex and association of the amplification probe, the hybridization complex is rolling-circle amplified to generate a cDNA nanoball (or amplicon) containing multiple copies of the cDNA. Techniques for rolling circle amplification (RCA) include linear RCA, a branched RCA, a dendritic RCA, or any combination thereof (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:el 18, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801, all of which are herein incorporated by reference in their entireties). Exemplary polymerases for use in RCA of target circRNAs include, e.g., Murine Leukemia Virus reverse transcriptase (MuLV RT), Moloney-Murine Leukemia Virus reverse transcriptase (M-MuLV RT), Maxima™ RNase H-minus reverse transcriptase, HiScript® III reverse transcriptase, ProtoScript® II reverse transcriptase, RevertAid™ H minus reverse transcriptase, and AMV reverse transcriptase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, US 2016/0024555, US 2016/0024555, US 2018/0251833 and US 2017/0219465, which are herein incorporated by reference in their entireties. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, the RCA template may comprise the target circRNA, or a part thereof, where the target analyte is circRNA, or it may be provided or generated as a proxy, or a marker, for the analyte. In some embodiments, different analytes are detected in situ in one or more cells using a RCA-based detection system, e.g., where the signal is provided by generating an RCA product from a circular RCA template which is provided or generated in the assay, and the RCA product is detected to detect the corresponding analyte. The RCA product may thus be regarded as a reporter which is detected to detect the target analyte, e.g., circRNA. However, the RCA template may also be regarded as a reporter for the target analyte; the RCA product is generated based on the RCA template, and comprises complementary copies of the RCA template. The RCA template determines the signal which is detected, and is thus indicative of the target analyte. As will be described in more detail below, the RCA template may be a circRNA, or a part or component of a circRNA.

III. Detecting

A. Detecting

The methods and compositions disclosed herein comprise detecting the RCA product in situ, e.g., in situ at a spatially localized position in the biological sample. This includes, in some instances, decoding a barcode that is a splice junction, using any of the methods or approaches for detection described herein.

Figure 4:
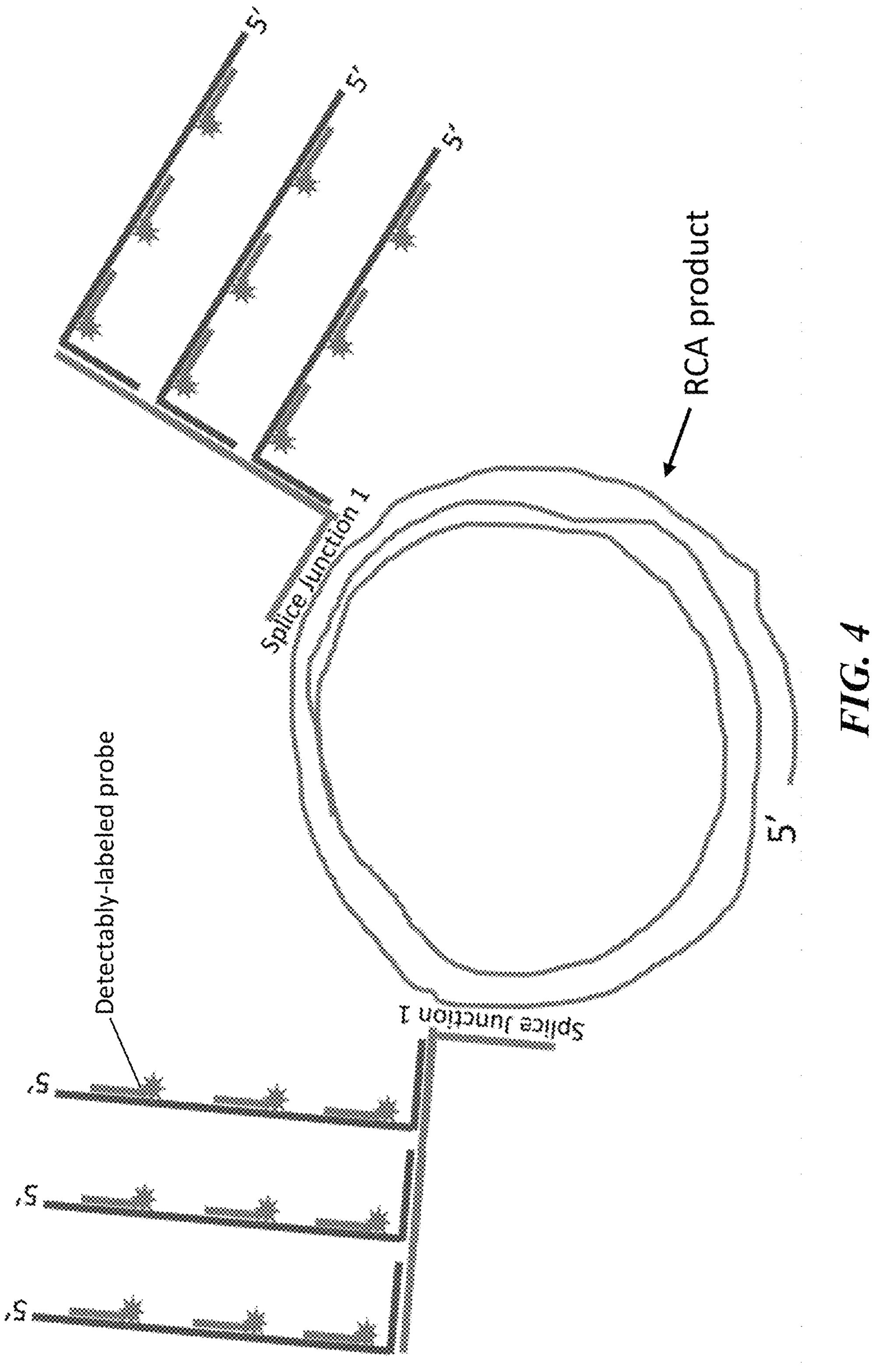
FIG. 4 depicts exemplary detection of an RCA product at marker sequences comprising splice junction 1, which is present in multiple copies in the RCA product, using detectably-labeled probes indirectly hybridized to the marker sequences of the RCA product via an assembly of branched structures in the form of two intermediate probes. The first intermediate probe directly hybridizes to the marker sequence corresponding to splice junction 1, the second intermediate probes directly hybridize to the first intermediate probe, and the detectably-labeled probes directly hybridize to the second intermediate probes.

In some instances, detecting the RCA product comprises contacting the biological sample with one or more detectably-labeled probes that directly or indirectly hybridize to the RCA product. In some embodiments, the one or more detectably-labeled probes directly hybridize to the RCA product. In some instances, detecting the RCA product can further comprise dehybridizing the one or more detectably-labeled probes from the rolling circle amplification product. In some embodiments, the contacting and dehybridizing steps can be repeated with the one or more detectably-labeled probes and/or one or more other detectably-labeled probes that directly or indirectly hybridize to the RCA product. In some embodiments, the one or more detectably-labeled probes indirectly hybridize to the RCA product via one or more intermediate probes, such as shown in FIG. 4.

Figure 2B:
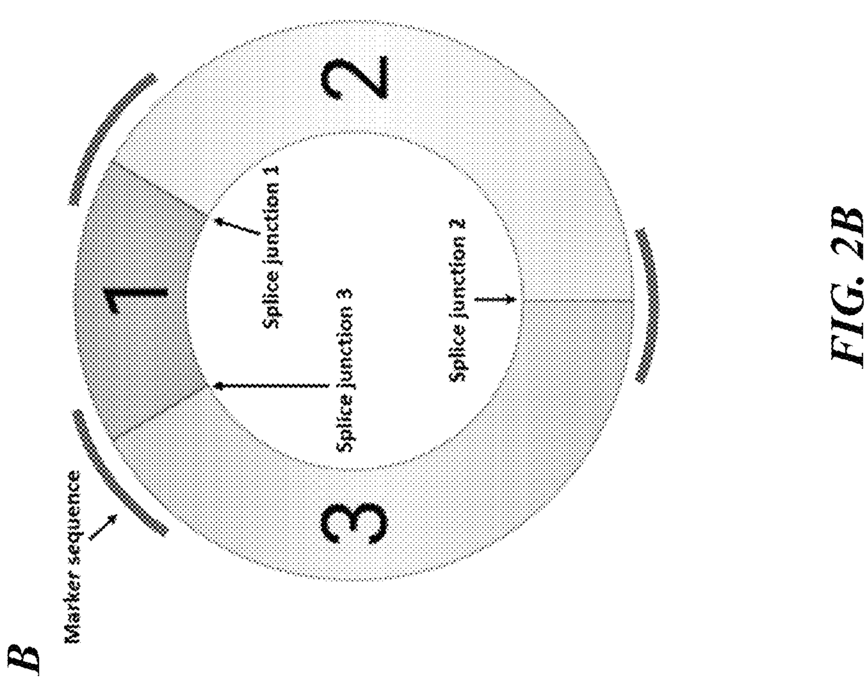
FIGS. 2A-2B depicts exemplary circRNAs having three or four splice junctions that can be used as barcodes.
Figure 2A:
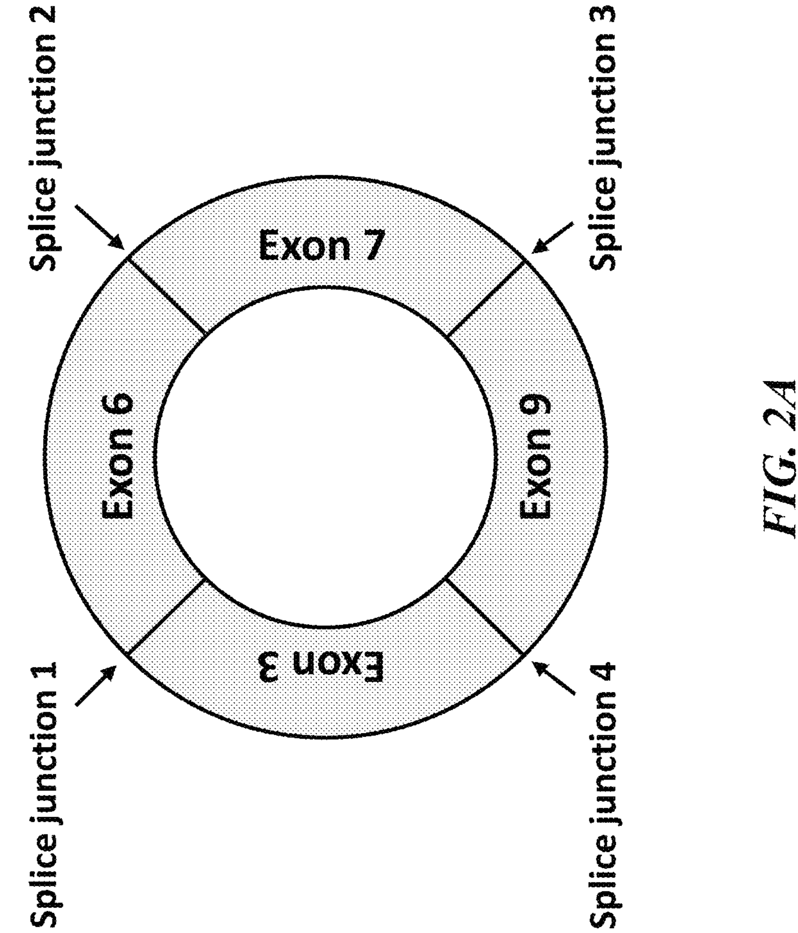

In some aspects, the provided methods involve analyzing, e.g., detecting or determining, one or more sequences present in the RCA product. In some embodiments, the one or more sequences present in the RCA product comprise one or more marker sequences (e.g., sequences that can be used to identify a circRNA or group of related circRNAs). The marker sequences, in some instances, each comprise a splice junction, such as shown in FIGS. 2A-2B. In some aspects, the circRNA comprises one, two, three, four, or five or more marker sequences each comprising a splice junction, wherein one of the marker sequences comprises a splice junction that is a back-splice junction. In some embodiments, a first marker sequence is common to a group of circRNAs, and a second marker sequence can identify variants within the group of circRNAs (e.g., alternative splice forms of the circRNAs). In some embodiments, the first marker sequence comprises a back-splice junction, and the second marker sequence comprises a splice junction present in one splice form of the circRNA but absent in another splice form of the circRNA. In some embodiments, the method comprises analyzing, e.g., detecting or determining, the first marker sequence comprising a back-splice junction at a spatially localized position in the biological sample. In some embodiments, the method comprises analyzing, e.g., detecting or determining, the second marker sequence at the spatially localized position in the biological sample.

In some aspects, the provided methods involve analyzing, e.g., detecting or determining, two or more sequences, e.g., marker sequences, present in the RCA product. In some embodiments, each of the two or more sequences present in the RCA product are different and correspond to different splice sites present in the corresponding circRNA. In some embodiments, the RCA product comprises multiple copies of a marker sequence. The number of copies of a marker sequence is not particularly limited. In some embodiments, the multiple copies of the marker sequence comprises two, three, four, or five or more copies of the marker sequence in the RCA product. In some instances, each of the multiple copies of a marker sequence present in the RCA product can be detected using any of the probes described herein, thereby allowing for signal amplification and enhanced detection. In some embodiments, the multiple copies of the marker sequence present in the RCA product are detected without further signal amplification in the biological sample.

In some instances, the method comprises contacting the biological sample with one or more detectably-labeled probes complementary to the marker sequence. In some instances, detecting the RCA product comprises detecting a signal associated with the one or more detectably-labeled probes. In some embodiments, the signal associated with the one or more detectably-labeled probes is amplified in situ in the biological sample. In some embodiments, the signal associated with the one or more detectably-labeled probes is not amplified in situ in the biological sample.

In some embodiments, the signal amplification of the signal associated with the one or more detectably-labeled probes comprises rolling circle amplification (RCA) of a probe that directly or indirectly binds to the RCA product; hybridization chain reaction (HCR) directly or indirectly on the RCA product; linear oligonucleotide hybridization chain reaction (LO-HCR) directly or indirectly on the RCA product; primer exchange reaction (PER) directly or indirectly on the RCA product; assembly of branched structures directly or indirectly on the RCA product; hybridization of a plurality of detectable probes directly or indirectly on the RCA product, or any combination thereof. In some embodiments, the signal amplification comprises rolling circle amplification (RCA) of a probe that directly or indirectly binds to the RCA product. In some embodiments, the signal amplification comprises hybridization chain reaction (HCR) directly or indirectly on the RCA product. In some embodiments, the signal amplification comprises linear oligonucleotide hybridization chain reaction (LO-HCR) directly or indirectly on the RCA product. In some embodiments, the signal amplification comprises primer exchange reaction (PER) directly or indirectly on the RCA product. In some embodiments, the signal amplification comprises assembly of branched structures directly or indirectly on the RCA product, such as depicted in FIG. 4. In some embodiments, the signal amplification comprises hybridization of a plurality of detectable probes directly or indirectly on the RCA product, or any combination thereof.

In some embodiments, the one or more marker sequences present in the RCA product are analyzed by sequencing all or a portion of the one or more marker sequences at a spatially localized position in the biological sample. In some instances, the sequencing comprises sequencing by hybridization, sequence by ligation, and/or fluorescent in situ sequencing. In some embodiments, the in situ hybridization comprises sequential fluorescent in situ hybridization. In some instances, detecting the RCA product comprises hybridization-based in situ sequencing (HybISS). See, e.g., Gyllborg et al., Nucleic Acids Res., 48(19):el 12 (2020), the content of which is herein incorporated by reference in its entirety.

In some embodiments, the method comprises detecting a first marker sequence (e.g., a complement of a first splice junction) in the RCA product. In some embodiments, the method further comprises detecting a second marker sequence (e.g., a complement of a second splice junction) in the RCA product. In some embodiments, the method further comprises detecting a third marker sequence (e.g., a complement of a third splice junction) in the RCA product. In some embodiments, detecting each marker sequence comprises binding a detectably labeled probe directly or indirectly to the marker sequence in the RCA product. In some embodiments, the method comprises removing the detectably labeled probe before hybridizing the next detectably labeled probe to the next marker sequence. In some embodiments, the method comprises cleaving a detectable label from the detectably labeled probe before hybridizing the next detectably labeled probe. For example, the detectable label can be attached to the detectably labeled probe via a cleavable thiol linker for removal of the detectable label. In some embodiments, the detectable label can be quenched before hybridization of the next detectably labeled probe.

In some embodiments, the detecting comprises detecting one or more marker sequences in the circRNA and/or the RCA product. Each of the one or more marker sequences can be a sequence of the circRNA (or a complement thereof present in the RCA product) that identifies the circRNA or RCA product individually or in combination with one or more other marker sequences. In some instances, one or more of the one or more marker sequences comprise a splice junction present in the circRNA, or a complement thereof present in the RCA product. In some instances, the circRNA and/or the RCA product comprises multiple marker sequences, wherein detecting a combination of the marker sequences identifies the circRNA, and wherein detecting the RCA product comprises detecting the combination of the marker sequences. In some embodiments, detecting two or more of the marker sequences identifies the circRNA. In some embodiments, detecting two, three, four, or five of the marker sequences identifies the circRNA. In some embodiments, detecting two, three, four, five, six, seven, eight, nine, or ten or more of the marker sequences identifies the circRNA. In some embodiments, detecting a marker sequence comprising the back-splice junction identifies the circRNA. In some embodiments, detecting a marker sequence comprising the back-splice junction in combination with one or more other marker sequences identifies the circRNA.

In some embodiments, a marker sequence is assigned a signal code sequence, and detecting the marker sequence comprises i) contacting the biological sample with a first detectable probe and a first detectably labeled oligonucleotide to generate a first complex comprising the first detectable probe hybridized to the marker sequence in the RCA product and the first detectably labeled oligonucleotide hybridized to the first detectable probe, wherein the first detectable probe comprises: a recognition sequence complementary to the marker sequence in the RCA product, and a first overhang sequence, and wherein the first detectably labeled oligonucleotide comprises: a sequence complementary to the first overhang sequence, and a first optically detectable moiety; ii) imaging the biological sample to detect a first signal from the first optically detectable moiety, wherein the first signal corresponds to a first signal code in the signal code sequence; iii) contacting the biological sample with a second detectable probe and a second detectably labeled oligonucleotide to generate a second complex comprising the second detectable probe hybridized to the marker sequence of the RCA product and the second detectably labeled oligonucleotide hybridized to the second detectable probe, wherein the second detectable probe comprises: a recognition sequence complementary to the marker sequence, and a second overhang sequence, and wherein the second detectably labeled oligonucleotide comprises: a sequence complementary to the second overhang sequence, and a second optically detectable moiety; and iv) imaging the biological sample to detect a second signal from the second optically detectable moiety, wherein the second signal corresponds to a second signal code in the signal code sequence, wherein the signal code sequence comprising at least the first signal code and the second signal code is determined at a location in the biological sample, thereby detecting the marker sequence (e.g., complement of a splice junction) in the RCA product and detecting the corresponding circRNA at the location in the biological sample.

In some aspects, the methods described herein comprise multiplex detection of a plurality of circRNAs at spatially localized positions in the biological sample. In some embodiments, the plurality of circRNAs are amplified by rolling circle amplification to generate a plurality of RCA products at their respective locations in the biological sample. In some embodiments, the plurality of circRNAs comprise different back-splice junction sequences that can be used as marker sequences to distinguish the different circRNAs. In some embodiments, the marker sequences are complements of the back-splice junctions present in the RCA products for the respective circRNAs, wherein each RCA product comprises multiple copies of the respective marker sequence. In some embodiments, one or more, or each of the marker sequences is assigned a signal code sequence and detected as described above (e.g., by sequential hybridization of detectable probes and imaging the sample, thereby determining the signal code sequence at a location in the biological sample). In some embodiments, the method comprises detecting a first marker sequence and a second marker sequence at the same position in the biological sample, wherein the combination of the first marker sequence and the second marker sequence (e.g., a first splice junction and a second splice junction) identifies the circRNA.

In some instances, one or more, or each, of the marker sequences are splice junctions present in the circRNA. In some instances, the multiple marker sequences being detected are multiple splice junctions present in the circRNA. The number of splice junctions in the multiple splice junctions is not limited and may vary depending on the circRNA and the splicing of its pre-mRNA. In some embodiments, the multiple splice junctions that can be detected comprise at least one, two, three, four, five, six, seven, eight, nine, or ten or more splice junctions. In some instances, the multiple splice junctions that can be detected comprises one, two, three, four, or five splice junctions. In some embodiments, each of the one or more marker sequences is a barcode sequence.

In some embodiments, detecting each of the one or more marker sequences individually or in combination with one or more other marker sequences identifies an isoform of circRNA. In some embodiments, the isoform of circRNA comprises a unique set of splice junctions created by pre-mRNA splicing that distinguishes it from one or more other isoforms of circRNA, e.g., one or more other isoforms of circRNA derived from the same gene. In some embodiments, detecting each of the one or more marker sequences, individually or in combination with one or more other marker sequences, identifies a circRNA comprising a specific splice junction(s), or identifies a circRNA isoform comprising a specific splice junction(s).

In any one of the embodiments herein, a sequence associated with the target circRNA or the RCA product or the probe(s), e.g., one or more marker sequences, can comprise one or more barcode sequences or complements thereof. In any one of the embodiments herein, the sequence of the rolling circle amplification product can comprise one or more marker sequences or complements thereof, each of which can be or comprise a barcode sequence. Accordingly, in any one of the embodiments herein, the sequence of the rolling circle amplification product can comprise one or more barcode sequences or complements thereof. In any one of the embodiments herein, the one or more barcode sequences can comprise a barcode sequence corresponding to the target circRNA or the RCA product. In any one of the embodiments herein, the one or more barcode sequences can comprise a barcode sequence corresponding to the sequence of interest, such as variant(s) of the circRNA of interest, which may differ in the way by which they were splice during pre-mRNA splicing. In some embodiments, the one or more barcode sequences or complements thereof are, or are comprised within, one or more marker sequences.

In some aspects, any of the RCA products or probe(s) described herein can comprise one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte, e.g., a circRNA or an RCA product, or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or UMI). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In some embodiments, marker sequences or barcodes or complements thereof (e.g., marker sequences or barcode sequences or complements thereof comprised by the RCA products or probes disclosed herein or products thereof) can be analyzed (e.g., detected or sequenced) using any suitable method or technique, including those described herein, such as sequencing by synthesis (SBS), sequencing by ligation (SBL), or sequencing by hybridization (SBH). In some instances, barcoding schemes and/or barcode detection schemes as described in RNA sequential probing of targets (RNA SPOTs), single-molecule fluorescent in situ hybridization (smFISH), multiplexed error-robust fluorescence in situ hybridization (MERFISH) or sequential fluorescence in situ hybridization (seqFISH+) can be used. In any of the preceding implementations, the methods provided herein can include analyzing the marker sequences or barcodes by sequential hybridization and detection with a plurality of labelled probes (e.g., detection probes (e.g., detection oligos) or barcode probes). In some instances, the marker or barcode detection steps can be performed as described in hybridization-based in situ sequencing (HybISS). In some instances, probes can be detected and analyzed (e.g., detected or sequenced) as performed in fluorescent in situ sequencing (FISSEQ), or as performed in the detection steps of the spatially-resolved transcript amplicon readout mapping (STARmap) method. In some instances, signals associated with an analyte, e.g., RCA product, can be detected as performed in sequential fluorescent in situ hybridization (seqFISH).

In some embodiments, in a barcode sequencing method, barcode sequences are detected for identification of other molecules including nucleic acid molecules (DNA or RNA) longer than the barcode sequences themselves, including circRNAs and RCA products, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and 20210164039, which are hereby incorporated by reference in their entirety.

In any one of the embodiments herein, instead of detecting the presence of oligonucleotides that hybridize directly to a target nucleic acid, e.g., a circRNA or RCA product, the methods disclosed herein include detecting the cleavage of a non-hybridized sequence of an oligonucleotide (for example, a duplex region) and further analyzing to determine the presence of absence of an analyte (for example, a circRNA or RCA product) of interest. In any one of the embodiments herein, the method includes determining all or part of the duplex region. In any one of the embodiments herein, the duplex region further includes a barcode sequence. When the duplex is cleaved, the duplex can be used to identify a hybridization and/or ligation event where the circularizable probe or the first and second nucleic acid probe undergo ligation. In some aspects, the determining all or part of the duplex region includes sequencing. In some instances, the duplex region can include a functional sequence. The functional sequence can be a primer sequence. The primer sequence can be used to amplify the duplex region or the stem-loop structure before cleavage, contemporaneously with cleavage, or after cleavage of the duplex region from the nucleic acid probe.

In any one of the embodiments herein, the detecting step can comprise contacting the biological sample with one or more detectably-labeled probes that directly or indirectly hybridize to the rolling circle amplification product, and dehybridizing the one or more detectably-labeled probes from the rolling circle amplification product. In any one of the embodiments herein, the contacting and dehybridizing steps can be repeated with the one or more detectably-labeled probes and/or one or more other detectably-labeled probes that directly or indirectly hybridize to the rolling circle amplification product.

In some embodiments, the one or more detectably-labeled probes indirectly hybridize to the RCA product. In some embodiments, detecting can comprise contacting the biological sample with one or more intermediate probes that directly or indirectly hybridize to the RCA product, wherein the one or more intermediate probes are detectable using the one or more detectably-labeled probes. In some embodiments, one or more first intermediate probes hybridize directly or indirectly to a marker sequence or barcode sequence in the RCA product. In some instances, one or more second intermediate probes directly or indirectly hybridize to one or more of the first intermediate probes. In some instances, one or more detectably-labeled probes directly or indirectly hybridize to one or more of the second intermediate probes. Accordingly, in some embodiments, one or more first intermediate probes hybridize directly or indirectly to a marker sequence or barcode sequence in the RCA product, one or more second intermediate probes directly or indirectly hybridize to one or more of the first intermediate probes, and one or more detectably-labeled probes directly or indirectly hybridize to one or more of the second intermediate probes.

In some embodiments, one or more first intermediate probes hybridize directly to a marker sequence or barcode sequence in the RCA product. In some instances, one or more second intermediate probes directly hybridize to one or more of the first intermediate probes. In some instances, one or more detectably-labeled probes directly hybridize to one or more of the second intermediate probes. Accordingly, in some embodiments, one or more first intermediate probes hybridize directly to a marker sequence or barcode sequence in the RCA product, one or more second intermediate probes directly hybridize to one or more of the first intermediate probes, and one or more detectably-labeled probes directly hybridize to one or more of the second intermediate probes.

In some embodiments, detecting can further comprise dehybridizing the one or more intermediate probes and/or the one or more detectably-labeled probes from the RCA product. In any one of the embodiments herein, the contacting and dehybridizing steps can be repeated with the one or more intermediate probes, the one or more detectably-labeled probes, one or more other intermediate probes, and/or one or more other detectably-labeled probes.

In some embodiments, the detection may be spatial, e.g., in two or three dimensions. In some embodiments, the detection may be spatial, e.g., in two or three dimensions, in a biological sample in situ. In some embodiments, the detection may be quantitative, e.g., the amount or concentration of a primary nucleic acid probe (and of a target nucleic acid) or a stem-loop structure may be determined. In some embodiments, the intermediate probes, the primary probes, the secondary probes, the higher order probes, and/or the detectably labeled probes may comprise any one of a variety of entities able to hybridize a nucleic acid, e.g., DNA.

In some embodiments, disclosed herein is a multiplexed assay where multiple targets (e.g., RCA products) are probed with multiple primary probes (e.g., circularizable primary probes, or one or more intermediate probes). In some embodiments, multiple secondary probes hybridizing to the primary barcodes (or complementary sequences thereof) are all hybridized at once, followed by sequential secondary barcode detection and decoding of the signals. In some embodiments, detection of barcodes or subsequences of the barcode can occur in a cyclic manner.

In some embodiments, a method for analyzing a region of interest in an RCA product of a circRNA is a multiplexed assay where multiple probes (e.g., circularizable probes, or one or more intermediate probes) are used to detect multiple regions of interest simultaneously (e.g., variations at the same location of an RCA product or at multiple sites corresponding to different splice sites). In some embodiments, one or more detections of one or more regions of interest may occur simultaneously. In some embodiments, one or more detections of one or more regions of interest may occur sequentially. In some embodiments, multiple circularizable probes of the same circularizable probe design are used to detect one or more regions of interest, using different barcodes associated with each region of interest. In some embodiments, multiple circularizable probes of different circularizable probe design are used to detect one or more regions of interest, using different barcodes (e.g., each barcode associated with a target nucleic acid or sequence thereof). In some embodiments, the one or more regions of interest are localized on the same molecule (e.g., RCA product).

In some embodiments, multiple intermediate probes of the same probe design are used to detect one or more regions of interest, e.g., one or more splice sites of interest or one or more marker sequences, using different barcodes associated with each region of interest, e.g., each splice site of interest or marker sequence. In some embodiments, multiple intermediate probes of different intermediate probe design are used to detect one or more regions of interest, e.g., one or more splice sites of interest or one or more marker sequences, using different barcodes (e.g., each barcode associated with a target nucleic acid or sequence thereof, such as a splice site of interest or marker sequence). In some embodiments, the one or more regions of interest, e.g., one or more splice sites of interest or one or more marker sequences, are localized on the same molecule (e.g., RCA product). In some embodiments, multiple primary probes of the same probe design are used to detect one or more regions of interest, e.g., one or more splice sites of interest or one or more marker sequences, using different barcodes associated with each region of interest, e.g., each splice site of interest or marker sequence. In some embodiments, multiple primary probes of different intermediate probe design are used to detect one or more regions of interest, e.g., one or more splice sites of interest or one or more marker sequences, using different barcodes (e.g., each barcode associated with a target nucleic acid or sequence thereof, such as a splice site of interest or marker sequence). In some embodiments, the one or more regions of interest, e.g., one or more splice sites of interest or one or more marker sequences, are localized on the same molecule (e.g., RCA product).

In some embodiments, the detection comprises providing detection probes, such as probes for performing a chain reaction that forms an amplification product, e.g., HCR. In some embodiments, the analysis comprises determining the sequence of all or a portion of the amplification product. In some embodiments, the analysis comprises detecting a sequence present in the amplification product. In some embodiments, the sequence of all or a portion of the amplification product is indicative of the identity of a region of interest in a target circRNA or RCA product thereof. In other embodiments, the provided methods involve analyzing, e.g., detecting or determining, one or more sequences present in the RCA product.

In some embodiments, a method disclosed herein may also comprise one or more signal amplification components. In some embodiments, the present disclosure relates to the detection of nucleic acids sequences in situ using probe hybridization and generation of amplified signals associated with the probes, wherein background signal is reduced and sensitivity is increased. In some embodiments, the RCA product generated using a method disclosed herein can be detected in with a method that comprises signal amplification.

Exemplary signal amplification methods include targeted deposition of detectable reactive molecules around the site of probe hybridization, targeted assembly of branched structures (e.g., bDNA or branched assay using locked nucleic acid (LNA)), programmed in situ growth of concatemers by enzymatic rolling circle amplification (RCA) (e.g., as described in US 2019/0055594 incorporated herein by reference), hybridization chain reaction, assembly of topologically catenated DNA structures using serial rounds of chemical ligation (clampFISH), signal amplification via hairpin-mediated concatemerization (e.g., as described in US 2020/0362398 incorporated herein by reference), e.g., primer exchange reactions such as signal amplification by exchange reaction (SABER) or SABER with DNA-Exchange (Exchange-SABER). In some embodiments, a non-enzymatic signal amplification method may be used.

The detectable reactive molecules may comprise tyramide, such as used in tyramide signal amplification (TSA) or multiplexed catalyzed reporter deposition (CARD)-FISH. In some embodiments, the detectable reactive molecule may be releasable and/or cleavable from a detectable label such as a fluorophore. In some embodiments, a method disclosed herein comprises multiplexed analysis of a biological sample comprising consecutive cycles of probe hybridization, fluorescence imaging, and signal removal, where the signal removal comprises removing the fluorophore from a fluorophore-labeled reactive molecule (e.g., tyramide). Exemplary detectable reactive reagents and methods are described in U.S. Pat. No. 6,828,109, US 2019/0376956, US 2019/0376956, US 2022/0026433, US 2022/0128565, and US 2021/0222234, all of which are incorporated herein by reference in their entireties.

In some embodiments, hybridization chain reaction (HCR) can be used for signal amplification. HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte, e.g., RCA product. HCR is described in detail in Dirks and Pierce, 2004, PNAS, 101(43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401, all of which are herein incorporated by reference in their entireties). HCR monomers typically comprise a hairpin, or other metastable nucleic acid structure. In the simplest form of HCR, two different types of stable hairpin monomer, referred to here as first and second HCR monomers, undergo a chain reaction of hybridization events to form a long nicked double-stranded DNA molecule when an initiator nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure may be known as the toehold region (or input domain). The first HCR monomers each further comprise a sequence which is complementary to a sequence in the exposed toehold region of the second HCR monomers. This sequence of complementarity in the first HCR monomers may be known as the interacting region (or output domain). Similarly, the second HCR monomers each comprise an interacting region (output domain), e.g. a sequence which is complementary to the exposed toehold region (input domain) of the first HCR monomers. In the absence of the HCR initiator, these interacting regions are protected by the secondary structure (e.g. they are not exposed), and thus the hairpin monomers are stable or kinetically trapped (e.g., metastable), and remain as monomers (e.g. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (e.g. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted (e.g. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridization to and invasion of a first HCR monomer. The first and second HCR monomers are designed to hybridize to one another are thus may be defined as cognate to one another. They are also cognate to a given HCR initiator sequence. HCR monomers which interact with one another (hybridize) may be described as a set of HCR monomers or an HCR monomer, or hairpin, system.

An HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR may comprise an interacting region which binds to the toehold region of a third HCR monomer; and each third HCR monomer may comprise an interacting region which binds to the toehold region of a first HCR monomer. The HCR polymerization reaction would then proceed as described above, except that the resulting product would be a polymer having a repeating unit of first, second and third monomers consecutively. Corresponding systems with larger numbers of sets of HCR monomers could readily be conceived. Branching HCR systems have also been devised and described (see, e.g., US 2022/0064697 incorporated herein by reference), and may be used in the methods herein.

In some embodiments, similar to HCR reactions that use hairpin monomers, linear oligo hybridization chain reaction (LO-HCR) can also be used for signal amplification. In some embodiments, the detecting an RCA product comprises (i) performing a linear oligo hybridization chain reaction (LO-HCR), wherein an initiator is contacted with a plurality of LO-HCR monomers of at least a first and a second species to generate a polymeric LO-HCR product hybridized to an RCA product, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the RCA product; and (ii) detecting the polymeric product, thereby detecting the RCA product. In some embodiments, the first species and/or the second species may not comprise a hairpin structure. In some embodiments, the plurality of LO-HCR monomers may not comprise a metastable secondary structure. In some embodiments, the LO-HCR polymer may not comprise a branched structure. In some embodiments, performing the linear oligo hybridization chain reaction comprises contacting the RCA product with the initiator to provide the initiator hybridized to the RCA product.

In some embodiments, detection of circRNA in situ includes combination of RCA with an assembly for branched signal amplification. In some embodiments, the assembly complex comprises an amplifier hybridized directly or indirectly (via one or more oligonucleotides) to a sequence of the RCA product. In some embodiments, the assembly includes one or more amplifiers each including an amplifier repeating sequence. In some aspects, the one or more amplifiers is labeled. Described herein is a method of using the aforementioned assembly, including for example, using the assembly in multiplexed error-robust fluorescent in situ hybridization (MERFISH) applications, with branched DNA amplification for signal readout. In some embodiments, the amplifier repeating sequence is about 5-30 nucleotides, and is repeated N times in the amplifier. In some embodiments, the amplifier repeating sequence is about 20 nucleotides, and is repeated at least two times in the amplifier. In some aspects, the one or more amplifier repeating sequence is labeled. For exemplary branched signal amplification, see e.g., U.S. Pat. Pub. No. US20200399689A1 and Xia et al., Multiplexed Detection of RNA using MERFISH and branched DNA amplification. Scientific Reports (2019), each of which is fully incorporated by reference herein.

In some embodiments, the RCA product can be detected with a method that comprises signal amplification by performing a primer exchange reaction (PER). In various embodiments, a primer with domain on its 3' end binds to a catalytic hairpin, and is extended with a new domain by a strand displacing polymerase. For example, a primer with domain 1 on its 3' ends binds to a catalytic hairpin, and is extended with a new domain 1 by a strand displacing polymerase, with repeated cycles generating a concatemer of repeated domain 1 sequences. In various embodiments, the strand displacing polymerase is Bst. In various embodiments, the catalytic hairpin includes a stopper which releases the strand displacing polymerase. In various embodiments, branch migration displaces the extended primer, which can then dissociate. In various embodiments, the primer undergoes repeated cycles to form a concatemer primer. In various embodiments, a plurality of concatemer primers is contacted with a sample comprising RCA products generated using methods described herein. In various embodiments, the RCA product may be contacted with a plurality of concatemer primers and a plurality of labeled probes. see e.g., U.S. Pat. Pub. No. US20190106733, which is incorporated herein by reference, for exemplary molecules and PER reaction components.

In some instances, detecting the RCA product comprises sequencing all or a portion of the amplification product and/or in situ hybridization to the amplification product. In some instances, detecting the RCA product comprises sequencing all or a portion of the amplification product, such as one or more portions comprising a splice site. In some instances, detecting the RCA product comprises in situ hybridization to the amplification product. In some embodiments, detecting the RCA product comprises sequencing the one or more marker sequences in the RCA product and/or in situ hybridization to the one or more marker sequences in the RCA product. In some embodiments, detecting the RCA product comprises sequencing the one or more marker sequences in the RCA product. n some embodiments, detecting the RCA product comprises in situ hybridization to the one or more marker sequences in the RCA product.

In some embodiments, the product or derivative of a first and second probe ligated together after hybridizing to the RCA product can be analyzed by sequencing. In some embodiments, the analysis and/or sequence determination comprises sequencing all or a portion of the amplification product or the probe(s) and/or in situ hybridization to the amplification product or the probe(s). In some embodiments, the sequencing step involves sequencing by hybridization, sequencing by ligation, and/or fluorescent in situ sequencing, hybridization-based in situ sequencing and/or wherein the in situ hybridization comprises sequential fluorescent in situ hybridization. In some embodiments, the analysis and/or sequence determination comprises detecting a polymer generated by a hybridization chain reaction (HCR) reaction, see e.g., US 2017/0009278, which is incorporated herein by reference, for exemplary probes and HCR reaction components. In some embodiments, the detection or determination comprises hybridizing to the amplification product a detection oligonucleotide labeled with a fluorophore, an isotope, a mass tag, or a combination thereof. In some embodiments, the detection or determination comprises imaging the amplification product. In some embodiments, the target circRNA is a circRNA in a tissue sample, and the detection or determination is performed when the target circRNA and/or the amplification product, e.g., RCA product, is in situ in the tissue sample.

In some aspects, provided herein are in situ assays using microscopy as a readout, e.g., nucleic acid sequencing, hybridization, or other detection or determination methods involving an optical readout. In some aspects, detection or determination of a sequence of one, two, three, four, five, or more nucleotides of a target nucleic acid is performed in situ in a cell in an intact tissue. In some aspects, the detection or determination is of a sequence associated with or indicative of an RCA product of a circRNA. In some aspects, detection or determination of a sequence is performed such that the localization of the target circRNA (or product or a derivative thereof associated with the target circRNA, e.g., an RCA product thereof) in the originating sample is detected. In some embodiments, the assay comprises detecting the presence or absence of an amplification product or a portion thereof (e.g., RCA product). In some embodiments, a method for spatially profiling target circRNAs, or the RCA products thereof, in a biological sample is provided. Methods, compositions, kits, devices, and systems for these in situ assays, comprising spatial genomics and transcriptomics assays, are provided. In some embodiments, a provided method is quantitative and preserves the spatial information within a tissue sample without physically isolating cells or using homogenates. In some embodiments, the present disclosure provides methods for high-throughput profiling of circRNAs in a large number of targets in situ, including various splice variants thereof, for detecting and/or quantifying circRNAs or their RCA products in cells, tissues, organs or organisms.

In some aspects, the provided methods comprise imaging the amplification product (e.g., amplicon), such as the RCA product, and/or one or more portions of the RCA product, for example, via binding of the detection probe and detecting the detectable label. In some embodiments, the detection probe comprises a detectable label that can be measured and quantitated. A label or detectable label can be a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

A fluorophore can comprise a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, Renilla luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. Autofluorescence can comprise background fluorescence (that can arise from a variety of sources, including aldehyde fixation, extracellular matrix components, red blood cells, lipofuscin, and the like), which is distinct from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

In some embodiments, a detectable probe comprising a sequence complementary to a detectably-labeled oligonucleotide can be used to detect one or more polynucleotide(s) and/or amplification products, e.g., RCA products, described herein. In some embodiments, the detectable probe hybridizes to the detectably-labeled oligonucleotide, forming a hybridization complex. In some embodiments, a detectable probe containing a detectable label can be used to detect one or more polynucleotide(s) and/or amplification products (e.g., amplicon), e.g., RCA products, described herein. In some embodiments, the methods involve incubating the detectable probe containing the detectable label with the sample, washing unbound detectable probe, and detecting the label, e.g., by imaging.

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as 1251, 35S, 14C, or 3H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991), all of which are herein incorporated by reference in their entireties. In some embodiments, exemplary techniques and methods methodologies applicable to the provided embodiments comprise those described in, for example, U.S. Pat. Nos. 4,757,141, 5,151,507 and 5,091,519, all of which are herein incorporated by reference in their entireties. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes), all of which are herein incorporated by reference in their entireties. Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264, all of which are herein incorporated by reference in their entireties. A fluorescent label can comprise a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-!2-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). Methods are suitable for custom synthesis of nucleotides having other fluorophores (See, Henegariu et al. (2000) Nature Biotechnol. 18:345, the content of which is herein incorporated by reference in its entirety).

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62, the content of which is herein incorporated by reference in its entirety).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. In some embodiments, the antibody can be an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or an polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and 5,192,782, all of which are herein incorporated by reference in their entireties. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/ or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any one of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The fluorescence microscope can be any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (e.g., reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequences in an RCA product of a circRNA can be analyzed in situ, e.g., by incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template, e.g., a nucleic acid sequence of an RCA product, such that the identities (e.g., nucleotide sequence) of the incorporated nucleotides or labeled primer extension products can be determined, and consequently, the nucleotide sequence of the corresponding RCA product. Aspects of in situ analysis are described, for example, in Mitra et al., (2003) Anal. Biochem. 320, 55-65, and Lee et al., (2014) Science, 343(6177), 1360-1363; US 2016/0024555; US 2019/0194709; U.S. Pat. Nos. 10,138,509; 10,494,662; 10,179,932, all of which are herein incorporated by reference in their entireties.

In some cases, sequencing can be performed after the circRNAs and/or RCA products are released from the biological sample. In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232, all of which are herein incorporated by reference in their entireties.

In some embodiments, sequencing can be performed by sequential fluorescence hybridization (e.g., sequencing by hybridization). Sequential fluorescence hybridization can involve sequential hybridization of detection probes comprising an oligonucleotide and a detectable label.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597, all of which are herein incorporated by reference in their entireties.

In some embodiments, the barcodes of the probes (e.g., barcodes of the RCA products or primary, secondary, or intermediate probes) or complements or products thereof are targeted by detectably labeled detection oligonucleotides, such as fluorescently labeled oligonucleotides. In some embodiments, the marker sequences of the RCA products generated from circRNAs in the biological sample are targeted by detectably labeled detection oligonucleotides, such as fluorescently labeled oligonucleotides. In some cases, the detectably labeled detection oligonucleotides hybridize directly to the marker sequences. In other embodiments, the detectably labeled detection oligonucleotides bind to the marker sequences indirectly (e.g., via one or more intermediate probes).

In some embodiments, one or more decoding schemes are used to decode the signals, such as fluorescence, for sequence determination. In any one of the embodiments herein, barcodes (e.g., primary and/or secondary barcode sequences) can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," Nature 568(7751):235-239 (2019); Chen et al., Science; 348(6233):aaa6090 (2015); Gyllborg et al., Nucleic Acids Res (2020) 48(19):el 12; U.S. Pat. No. 10,457,980 B2; US 2016/0369329 A1; US 2021/0017587; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004), each of which is fully incorporated by reference herein.

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181, all of which are herein incorporated by reference in their entireties.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

IV. Samples

Provided herein are methods that may be used for the identification of circRNAs of interest, for example, for the spatial identification of a circRNA of interest in situ, in a sample of interest, e.g., by detecting an RCA product of the circRNA.

A. Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can include nucleic acids (such as DNA or RNA), proteins/polypeptides, carbohydrates, and/or lipids. The biological sample can be obtained as a tissue sample, such as a tissue section, biopsy, a core biopsy, a cell pellet, a cell block, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include circRNA embedded in a 3D matrix. In some embodiments, amplicons (e.g., rolling circle amplification products) derived from or associated with circRNA can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, circRNAs, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. In some embodiments, the biological sample can be a fresh tissue sample. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 μm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 μm. Thicker sections can also be used if desired or convenient, e.g., at least 70, 80, 90, or 100 μm or more. Typically, the thickness of a tissue section is between 1-100 μm, 1-50 μm, 5-35 μm, 1-30 μm, 1-25 μm, 1-20 μm, 1-15 μm, 1-10 μm, 2-8 μm, 3-7 μm, or 4-6 μm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (e.g., postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a probe (e.g., a padlock probe).

In some embodiments, one or more post-fixing step is performed after contacting a sample with a binding or labeling agent (e.g., an antibody or antigen binding fragment thereof) for a non-nucleic acid analyte such as a protein analyte. The labeling agent can comprise a nucleic acid molecule (e.g., reporter oligonucleotide) comprising a sequence corresponding to the labeling agent and therefore corresponds to (e.g., uniquely identifies) the analyte. In some embodiments, the labeling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other suitable hydrogel-formation method.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 m to about 2 mm.

Additional methods and aspects of hydrogel embedding of biological samples are described for example in Chen et al., Science 347(6221):543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Any suitable methods of destaining or discoloring a biological sample may be utilized and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem.*

*Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in, e.g., Chen et al., Science 347(6221):543-548, 2015 and U.S. Pat. No. 10,059,990, which are herein incorporated by reference in their entireties.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. sDNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., *Nat. Methods* 13:679-684, 2016 and U.S. Pat. No. 10,059,990, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible or irreversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other suitable hydrogel-formation method. A hydrogel may include a macromolecular polymer gel including a network. In some embodiments, within the network, some polymer chains can be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labeling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to open up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, e.g., to generate cDNA, thereby selectively enriching these RNAs.

In some aspects, when two or more analytes are analyzed, a first and second probe that is specific for (e.g., specifically hybridizes to) each RNA or cDNA analyte can be used. For example, in some embodiments of the methods provided herein, templated ligation is used to detect gene expression in a biological sample. An analyte of interest (such as a protein), bound by a labeling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include extension or amplification of templated ligation products (e.g., by rolling circle amplification of a circular product generated in a templated ligation reaction).

A biological sample may comprise one or a plurality of analytes, e.g., circRNAs or RCA products, of interest. Methods for performing multiplexed assays to analyze two or more different analytes, e.g., circRNAs or RCA products, in a single biological sample are provided.

V. Compositions, Kits, and Systems

Also provided herein is a composition comprising any of the primers described herein, and/or any target circRNA described herein, and/or any RCA product described herein, and/or any of the probes as described herein, or any combination thereof.

Also provided herein is a composition comprising an RCA product generated using any of the amplification techniques described herein, e.g., RCA. In some embodiments, the composition comprises an RCA product generated by performing RCA of any of the target circRNAs described herein using any of the methods described herein.

Also provided herein is a kit comprising any of the probes described herein for use in a method for analyzing a biological sample, comprising (a) contacting a biological sample with a primer, wherein the primer hybridizes to a target sequence in a target circRNA; (b) using a reverse transcriptase to perform rolling circle amplification (RCA) of the circRNA, thereby generating an RCA product comprising multiple complementary copies of the circRNA; and (c) detecting the RCA product in situ at a spatially localized position in the biological sample. In some embodiments, the kit further comprises instructions for use.

Also provided herein is a kit comprising any of the probes described herein for use in a method for analyzing a biological sample, comprise (a) digesting linear RNA in the sample using RNase R; (b) contacting the biological sample with a primer, wherein the primer hybridizes to a target sequence in a target circular RNA (circRNA), wherein the target sequence comprises a back-splice junction; (c) using a reverse transcriptase having strand displacing activity to perform rolling circle amplification (RCA) of the circRNA, thereby generating an RCA product comprising multiple complementary copies of the circRNA in the biological sample; and (d) detecting the RCA product in situ at a spatially localized position in the biological sample, wherein detecting the RCA product comprises detecting one or more marker sequences comprising a complement of a splice junction present in the circRNA. In some embodiments, the kit further comprises instructions for use.

VI. Opto-Fluidic Instruments for Analysis of Biological Samples

Provided herein is an instrument having integrated optics and fluidics modules (an "opto-fluidic instrument" or "opto-fluidic system") for detecting target molecules (e.g., circular RNAs and other nucleic acids, proteins, antibodies, etc.) in biological samples (e.g., one or more cells or a tissue sample) as described herein. In an opto-fluidic instrument, the fluidics module is configured to deliver one or more reagents (e.g., detectably labeled probes) to the biological sample and/or remove spent reagents therefrom. Additionally, the optics module is configured to illuminate the biological sample with light having one or more spectral emission curves (over a range of wavelengths) and subsequently capture one or more images of emitted light signals from the biological sample during one or more probing cycles (e.g., as described in Section III). In various embodiments, the captured images may be processed in real time and/or at a later time to determine the presence of the one or more target molecules in the biological sample, as well as three-dimensional position information associated with each detected target molecule. Additionally, the opto-fluidics instrument includes a sample module configured to receive (and, optionally, secure) one or more biological samples. In some instances, the sample module includes an X-Y stage configured to move the biological sample along an X-Y plane (e.g., perpendicular to an objective lens of the optics module).

In various embodiments, the opto-fluidic instrument is configured to analyze one or more RNA substrates (e.g., circRNAs) in their naturally occurring place (i.e., in situ) within the biological sample. For example, an opto-fluidic instrument may be an in-situ analysis system used to analyze a biological sample and detect target molecules including but not limited to DNA, RNA, proteins, antibodies, and/or the like. The opto-fluidic instrument can be used to detect an RCA product generated from a circRNA in the biological sample in situ at a spatially localized position in the biological sample (e.g., at a localized position in three dimensions).

It is to be noted that, although the above discussion relates to an opto-fluidic instrument that can be used for in situ target molecule detection via probe hybridization (e.g., detection of a RCA product generated from a circRNA), the discussion herein equally applies to any opto-fluidic instrument that employs any imaging or target molecule detection technique. That is, for example, an opto-fluidic instrument may include a fluidics module that includes fluids needed for establishing the experimental conditions required for the probing of target molecules in the sample. Further, such an opto-fluidic instrument may also include a sample module configured to receive the sample, and an optics module including an imaging system for illuminating (e.g., exciting one or more fluorescent probes within the sample) and/or imaging light signals received from the probed sample. The in-situ analysis system may also include other ancillary modules configured to facilitate the operation of the opto-fluidic instrument, such as, but not limited to, cooling systems, motion calibration systems, etc.

Figure 5:
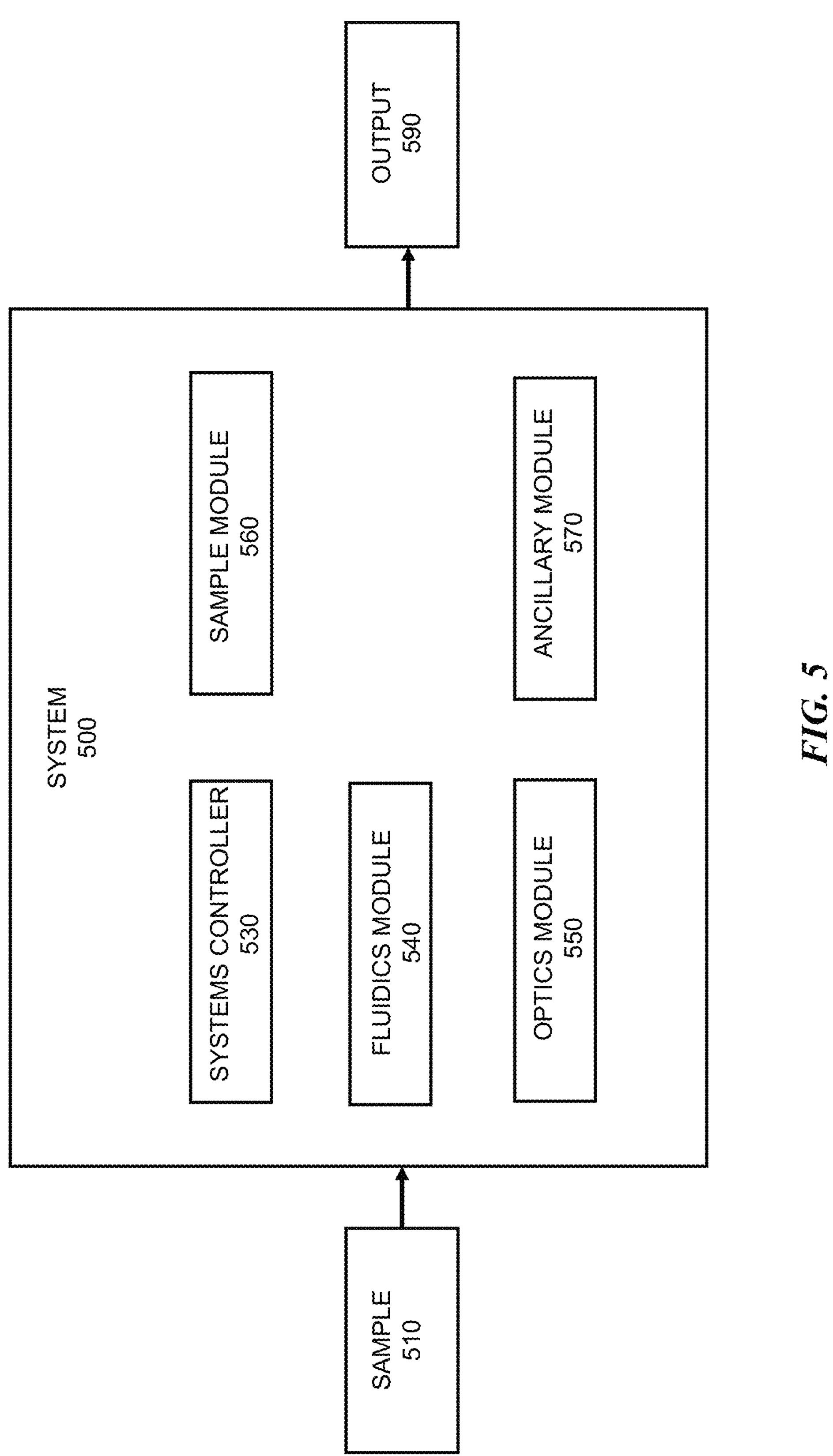
FIG. 5 is an example workflow of analysis of a biological sample (e.g., a cell or tissue sample) using an opto-fluidic instrument, according to various embodiments.

FIG. 5 shows an example workflow of analysis of a biological sample 510 (e.g., cell or tissue sample) using an opto-fluidic instrument 520, according to various embodiments. In various embodiments, the sample 510 can be a biological sample (e.g., a tissue) that includes molecules such as DNA, RNA, proteins, antibodies, etc. For example, the sample 510 can be a sectioned tissue that is treated to access the RNA thereof for rolling circle amplification and labeling with any of the probes described herein (e.g., any of the Samples described in Section IV).

In various embodiments, the sample 510 may be placed in the opto-fluidic instrument 520 for analysis and detection of the molecules in the sample 510. In various embodiments, the opto-fluidic instrument 520 can be a system configured to facilitate the experimental conditions conducive for the detection of the target molecules. For example, the opto-fluidic instrument 520 can include a fluidics module 540, an optics module 550, a sample module 560, and an ancillary module 570, and these modules may be operated by a system controller 530 to create the experimental conditions for the probing of the RCA products generated from circRNA molecules in situ in the sample 510, as well as to facilitate the imaging of the probed sample (e.g., by an imaging system of the optics module 550). In various embodiments, the various modules of the opto-fluidic instrument 520 may be separate components in communication with each other, or at least some of them may be integrated together.

In various embodiments, the sample module 560 may be configured to receive the sample 510 into the opto-fluidic instrument 520. For instance, the sample module 560 may include a sample interface module (SIM) that is configured to receive a sample device (e.g., cassette) onto which the sample 510 can be deposited. That is, the sample 510 may be placed in the opto-fluidic instrument 520 by depositing the sample 510 (e.g., the sectioned tissue) on a sample device that is then inserted into the SIM of the sample module 560. In some instances, the sample module 560 may also include an X-Y stage onto which the SIM is mounted. The X-Y stage may be configured to move the SIM mounted thereon (e.g., and as such the sample device containing the sample 510 inserted therein) in perpendicular directions along the two-dimensional (2D) plane of the opto-fluidic instrument 520.

The experimental conditions that are conducive for the detection of the molecules in the sample 510 may depend on the target molecule detection technique that is employed by the opto-fluidic instrument 520. For example, in various embodiments, the opto-fluidic instrument 520 can be a system that is configured to detect molecules in the sample 510 via hybridization of probes. In such cases, the experimental conditions can include molecule hybridization conditions that result in the intensity of hybridization of the target molecule (e.g., RCA product generated from a circRNA in the biological sample) to a probe (e.g., oligonucleotide) being significantly higher when the probe sequence is complementary to the target molecule than when there is a single-base mismatch. The hybridization conditions include the preparation of the sample 510 using reagents such as washing/stripping reagents, hybridizing reagents, etc., and such reagents may be provided by the fluidics module 540.

In various embodiments, the fluidics module 540 may include one or more components that may be used for storing the reagents, as well as for transporting said reagents to and from the sample device containing the sample 510. For example, the fluidics module 540 may include reservoirs configured to store the reagents, as well as a waste container configured for collecting the reagents (e.g., and other waste) after use by the opto-fluidic instrument 520 to analyze and detect the molecules of the sample 510. Further, the fluidics module 540 may also include pumps, tubes, pipettes, etc., that are configured to facilitate the transport of the reagent to the sample device (e.g., and as such the sample 510). For instance, the fluidics module 540 may include pumps ("reagent pumps") that are configured to pump washing/stripping reagents to the sample device for use in washing/stripping the sample 510 (e.g., as well as other washing functions such as washing an objective lens of the imaging system of the optics module 550).

In various embodiments, the ancillary module 570 can be a cooling system of the opto-fluidic instrument 520, and the cooling system may include a network of coolant-carrying tubes that are configured to transport coolants to various modules of the opto-fluidic instrument 520 for regulating the temperatures thereof. In such cases, the fluidics module 540 may include coolant reservoirs for storing the coolants and pumps (e.g., "coolant pumps") for generating a pressure differential, thereby forcing the coolants to flow from the reservoirs to the various modules of the opto-fluidic instrument 520 via the coolant-carrying tubes. In some instances, the fluidics module 540 may include returning coolant reservoirs that may be configured to receive and store returning coolants, i.e., heated coolants flowing back into the returning coolant reservoirs after absorbing heat discharged by the various modules of the opto-fluidic instrument 520. In such cases, the fluidics module 540 may also include cooling fans that are configured to force air (e.g., cool and/or ambient air) into the returning coolant reservoirs to cool the heated coolants stored therein. In some instance, the fluidics module 540 may also include cooling fans that are configured to force air directly into a component of the opto-fluidic instrument 520 so as to cool said component. For example, the fluidics module 540 may include cooling fans that are configured to direct cool or ambient air into the system controller 530 to cool the same.

As discussed above, the opto-fluidic instrument 520 may include an optics module 250 which include the various optical components of the opto-fluidic instrument 520, such as but not limited to a camera, an illumination module (e.g., LEDs), an objective lens, and/or the like. The optics module 550 may include a fluorescence imaging system that is configured to image the fluorescence emitted by the probes (e.g., oligonucleotides) in the sample 510 after the probes are excited by light from the illumination module of the optics module 550.

In some instances, the optics module 550 may also include an optical frame onto which the camera, the illumination module, and/or the X-Y stage of the sample module 560 may be mounted.

In various embodiments, the system controller 530 may be configured to control the operations of the opto-fluidic instrument 520 (e.g., and the operations of one or more modules thereof). In some instances, the system controller 530 may take various forms, including a processor, a single computer (or computer system), or multiple computers in communication with each other. In various embodiments, the system controller 530 may be communicatively coupled with data storage, set of input devices, display system, or a combination thereof. In some cases, some or all of these components may be considered to be part of or otherwise integrated with the system controller 530, may be separate components in communication with each other, or may be integrated together. In other examples, the system controller 530 can be, or may be in communication with, a cloud computing platform.

In various embodiments, the opto-fluidic instrument 520 may analyze the sample 510 and may generate the output 590 that includes indications of the presence of the target molecules in the sample 510. For instance, with respect to the example embodiment discussed above where the opto-fluidic instrument 520 employs a hybridization technique for detecting molecules, the opto-fluidic instrument 520 may cause the sample 510 to undergo successive rounds of detectably labeled probe hybridization (e.g., using two or more sets of fluorescent probes, where each set of fluorescent probes is excited by a different color channel) and be imaged to detect target molecules in the probed sample 510. In such cases, the output 590 may include optical signatures (e.g., a codeword) specific to each circRNA, which allow the identification of the circRNA.

VI. Terminology

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte, e.g., circRNA or RCA product, in a sample). A barcode can be part of an analyte, e.g., circRNA or RCA product, or independent of an analyte. A barcode can be attached to an analyte, e.g., a circRNA or an RCA product. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be or comprise a sequence comprising a splice junction in a target circRNA or an RCA product. A barcode can be attached to an analyte, e.g., a circRNA or an RCA product, or to another moiety or structure in a reversible or irreversible manner. A barcode can be added to, for example, a fragment of a deoxyribonucleic acid (DNA) or ribonucleic acid (RNA) sample before or during sequencing of the sample. A barcode can be a marker sequence, such as the marker sequences or one or more marker sequences as described herein, e.g., a complement of a splice junction, including a back-splice junction.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate, suitable backbone linkage including any of a variety. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of suitable analogs of these sugar moieties. A nucleic acid can include suitable native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Any suitable non-native bases that can be included in a nucleic acid or nucleotide may be utilized.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (e.g., can be oligoribonucleotides) and/or deoxyribonucleotide monomers (e.g., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

A "primer extension" refers to any method where two nucleic acid sequences become linked (e.g., hybridized) by an overlap of their respective terminal complementary nucleic acid sequences (e.g., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis.

(ix) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202; 4,683,195; 4,800,159; 4,965,188; and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments, the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oNTM DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (e.g., quantitative PCR or qPCR), using suitable techniques, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(x) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay, or an analyte, e.g., a circRNA or RCA product. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. For example, detectably labelled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18 (5)), DIDS, Dil (DilC18(3)), DiO (DiOC18(3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo- 4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/P0-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are suitable to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLES

The following examples are included for illustrative purposes only and are not intended to limit the scope of the present disclosure.

Example 1: In Situ Analysis of Circular RNA (circRNA) in a Biological Sample Using Rolling Circle Amplification (RCA) Followed by Detection This example describes exemplary methods for detecting for detecting a circular RNA (circRNA) in situ following the use of rolling circle amplification (RCA) of a target circRNA in a biological sample. In some aspects, the presence and/or relative abundance of circRNAs and their variant isoforms, e.g., due to alternative pre-mRNA splicing, can be detected by detecting one or more unique marker sequences in RCA products of the circRNAs, which can act as unique barcodes for decoding the RCA products.

A biological sample, e.g., a processed or cleared biological sample, a tissue sample, a sample embedded in a hydrogel, etc.) that includes a circRNA is prepared. As shown in FIG. 1, a target circRNA from a gene of interest can exist in multiple variant isoforms depending on the pre-mRNA splicing involved. For instance, as shown in FIG. 1, a target circRNA for a particular gene can include only exon 2, or can include only exons 1, 2, and 3, or can include only exons 3 and 4, as a result of alternative splicing.

Figure 3B:
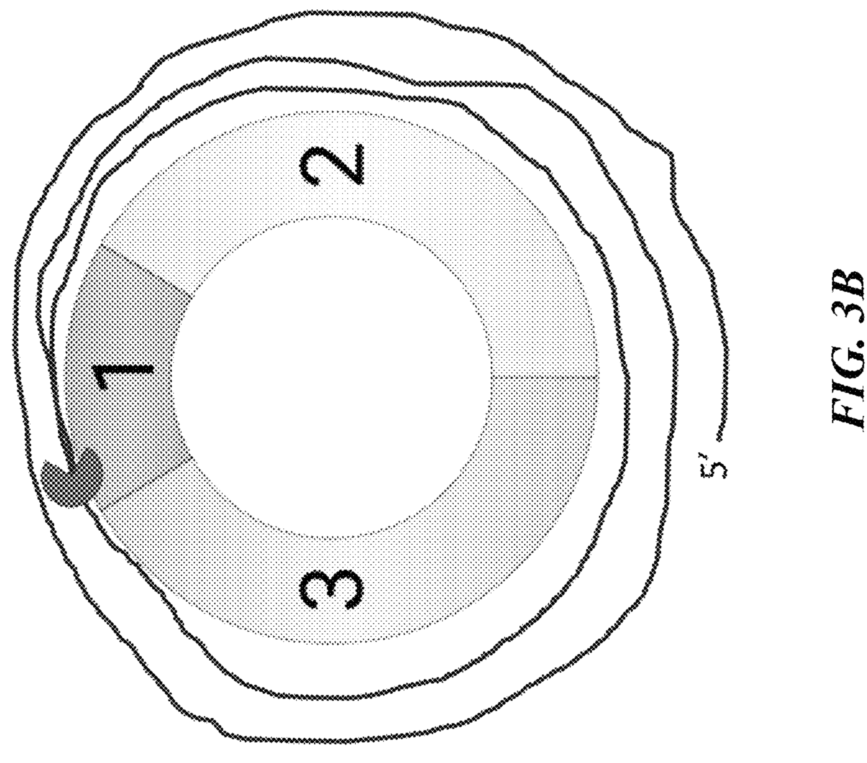
FIGS. 3A-3B depicts exemplary rolling circle amplification (RCA) of an exemplary circRNA having three splice junctions.
Figure 3A:
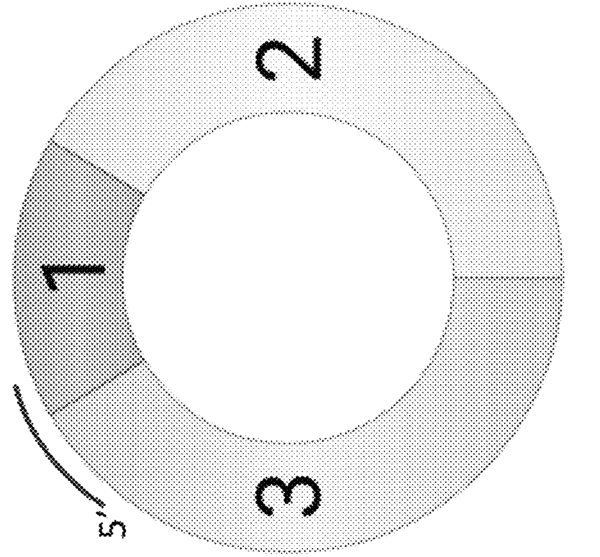

The sample is contacted with a primer that hybridizes to a target sequence in a target circRNA. The target sequence that the primer hybridizes to can include a splice junction. For instance, as shown in FIGS. 2A and 2B, a circRNA can include multiple splice junctions generated by pre-mRNA splicing. For circRNA, these splice junctions include a back-splice junction that is generated by a downstream 5' splice site joining to an upstream 3' splice site during pre-mRNA splicing, thereby being unique to circRNA as compared to their linear mRNA cognates. In FIG. 2A, the back-splice junction is splice junction 4, and in FIG. 2B, the back-splice junction is splice junction 3. In some examples, the target sequence that the primer hybridizes to includes the back-splice junction, as depicted in FIG. 3A. The sample is then incubated under conditions optimized for RCA of the target circRNA. RCA is performed using a reverse transcriptase, e.g., a Murine Leukemia Virus Reverse Transcriptase (MuLV RT) or a derivative thereof or a Moloney-Murine Leukemia Virus Reverse Transcriptase (M-MuLV RT) or a derivative thereof, thereby generating an RCA product comprising multiple complementary copies of the circRNA, as depicted in FIG. 3B.

In some examples, the method further includes contacting the sample with an RNase for digesting linear RNA in the sample, e.g., an exonuclease, such as RNase R, which can occur prior to, simultaneously with, or after the sample is contacted with the primer and/or the RCA is performed. Contacting the biological sample with an RNase, such as RNase R, results in the selective degradation of linear mRNA cognates of the circRNA, while leaving the circRNA intact, thereby advantageously reducing or eliminating background noise and enriching for circRNA prior to detection.

The RCA product is then detected in situ at a spatially localized position in the biological sample. For instance, as shown in FIG. 4, the RCA product can be detected using detectably-labeled probes that hybridize to the RCA product indirectly via an assembly of branched structures, e.g., intermediate probes, directly or indirectly on the RCA product, thereby amplifying the signal and allowing for a greatly increased signal from the RCA product.

The present disclosure is not intended to be limited in scope to the particular disclosed embodiments, which are provided, for example, to illustrate various aspects of the present disclosure. Various modifications to the compositions and methods described will become apparent from the description and teachings herein. Such variations may be practiced without departing from the true scope and spirit of the disclosure and are intended to fall within the scope of the present disclosure.

What is claimed is:

1. A method for analyzing a biological sample, comprising:
- contacting the biological sample with a primer, wherein the primer hybridizes to a target sequence in a target circular RNA (circRNA);
- using a reverse transcriptase to perform rolling circle amplification (RCA) of the circRNA, thereby generating an RCA product comprising multiple complementary copies of the circRNA; and
- detecting the RCA product in situ at a spatially localized position in the biological sample;
- wherein the circRNA and the RCA product comprise multiple marker sequences, wherein the combination of the marker sequences identifies the circRNA, and wherein detecting the RCA product comprises detecting the combination of the marker sequences.

2. The method of claim 1, further comprising contacting the sample with an RNase for digesting linear RNA in the sample.

3. The method of claim 2, wherein the RNase is an exonuclease.

4. The method of claim 2, wherein the RNase is RNase R.

5. The method of claim 1, wherein:
- the reverse transcriptase is a DNA strand-displacing reverse transcriptase; and/or
- the reverse transcriptase lacks RNase H activity.

6. The method of claim 1, wherein the reverse transcriptase is a Murine Leukemia Virus reverse transcriptase (MuL V RT) or a derivative thereof.

7. The method of claim 1, wherein the reverse transcriptase is a Moloney-murine leukemia virus reverse transcriptase (M-MuLV RT) or a derivative thereof.

8. The method of claim 1, wherein the target sequence comprises a splice junction in the circRNA.

9. The method of claim 8, wherein the splice junction is a back-splice junction, wherein the back-splice junction is generated by back-splicing, and wherein back-splicing comprises splicing of a pre-mRNA, wherein a downstream 5' splice site is joined to an upstream 3' splice site, thereby generating the circRNA.

10. The method of claim 1, wherein one or more of the marker sequences comprise a splice junction present in the circRNA, or a complement thereof present in the RCA product.

11. The method of claim 1, wherein the multiple marker sequences are multiple splice junctions present in the circRNA.

12. The method of claim 11, wherein the multiple splice junctions comprise a back-splice junction.

13. The method of claim 1, wherein detecting the RCA product comprises contacting the biological sample with one or more detectably-labeled probes that directly or indirectly hybridize to the RCA product.

14. A method for analyzing a biological sample, comprising:
- digesting linear RNA in the sample using RNase R;
- contacting the biological sample with a primer, wherein the primer hybridizes to a target sequence in a target circular RNA (circRNA), wherein the target sequence comprises a back-splice junction;
- using a reverse transcriptase having strand displacing activity to perform rolling circle amplification (RCA) of the circRNA, thereby generating an RCA product comprising multiple complementary copies of the circRNA in the biological sample; and
- detecting the RCA product in situ at a spatially localized position in the biological sample, wherein detecting the RCA product comprises detecting multiple marker sequences each comprising a complement of a splice junction present in the circRNA.

15. The method of claim 14, wherein detecting the RCA product comprises:
- detecting a signal associated with the one or more detectably-labeled probes; or
- sequencing all or a portion of the RCA product and/or in situ hybridization of the RCA product.

16. The method of claim 15, wherein the signal associated with the one or more detectably-labeled probes is amplified in situ in the biological sample.

17. The method of claim 16, wherein the signal amplification comprises rolling circle amplification (RCA) of a probe that directly or indirectly binds to the RCA product; hybridization chain reaction (HCR) directly or indirectly on the RCA product; linear oligonucleotide hybridization chain reaction (LO-HCR) directly or indirectly on the RCA product; primer exchange reaction (PER) directly or indirectly on the RCA product; assembly of branched structures directly or indirectly on the RCA product; hybridization of a plurality of detectable probes directly or indirectly on the RCA product, or any combination thereof.

18. The method of claim 15, wherein:
- the sequencing comprises sequencing by hybridization, sequencing by ligation, and/or fluorescent in situ sequencing; or
- the in situ hybridization comprises sequential fluorescent in situ hybridization.

19. The method of claim 14, wherein the splice junction of the multiple marker sequences comprises a back-splice junction.

* * * * *